US005728553A

United States Patent [19]
Goodey et al.

[11] Patent Number: 5,728,553
[45] Date of Patent: Mar. 17, 1998

[54] HIGH PURITY ALBUMIN AND METHOD OF PRODUCING

[75] Inventors: Andrew R. Goodey, Mapperley Park; Darrell Sleep, West Bridgford; Hendrik van Urk, Radcliffe-on-Trent; Stephen Berezenko, Hucknall; John R. Woodrow; Richard A. Johnson, both of West Bridgford; Patricia C. Wood, Burton-on-Trent; Steven J. Burton, Orton Brimbles; Alan V. Quirk, Loughborough; David St. J. Coghlan, Beeston; Mark J. Wilson, Cottenham, all of United Kingdom

[73] Assignee: Delta Biotechnology Limited, Nottingham, United Kingdom

[21] Appl. No.: 378,859

[22] Filed: May 25, 1995

Related U.S. Application Data

[63] Continuation-in-part of Ser. No. 265,972, Jun. 27, 1994, abandoned, which is a continuation of Ser. No. 949,601, Sep. 23, 1992, abandoned.

[51] Int. Cl.$^6$ ............... C12N 15/14; C07K 14/765; B01J 41/06; B01J 39/06
[52] U.S. Cl. ............... 435/69.6; 530/363; 530/364; 530/413; 530/414; 530/416; 530/417
[58] Field of Search ............... 435/69.6; 514/12; 530/363, 364, 412, 413, 416, 417, 414

[56] References Cited

U.S. PATENT DOCUMENTS

| | | | |
|---|---|---|---|
| 4,222,934 | 9/1980 | Hao | 530/364 |
| 4,350,156 | 9/1982 | Malchesky et al. | 604/6 |
| 4,675,384 | 6/1987 | Dromard et al. | 530/364 |
| 4,748,120 | 5/1988 | Weisenhahn | 435/173.3 |
| 4,990,447 | 2/1991 | König | 435/71.1 |
| 5,250,662 | 10/1993 | Chang | 530/364 |
| 5,330,901 | 7/1994 | Prevatt et al. | 435/69.6 |
| 5,440,018 | 8/1995 | Ohmura et al. | 530/363 |
| 5,612,196 | 3/1997 | Becquart et al. | 435/69.6 |

FOREIGN PATENT DOCUMENTS

| | | |
|---|---|---|
| 73 646 | 3/1983 | European Pat. Off. . |
| 244 998 | 11/1987 | European Pat. Off. . |
| 357 857 | 3/1990 | European Pat. Off. . |
| 367 220 | 5/1990 | European Pat. Off. . |
| 428 758 | 5/1991 | European Pat. Off. . |
| 452 753 | 10/1991 | European Pat. Off. . |
| 464 590 | 1/1992 | European Pat. Off. . |
| 0524681A1 | 1/1993 | European Pat. Off. . |
| 63/083100 | 4/1988 | Japan . |
| 90/05533 | 5/1990 | WIPO . |
| 92/09303 | 11/1990 | WIPO . |

OTHER PUBLICATIONS

Quirk et al. "Production of Recombinant Human Serum Albumin . . . "Biotech and Applied Biochemistry, 11: pp. 273–287 (1989).
Travis et al. "Isolation of Albumin from Whole Human Plasma . . . " Biochem. J. 157: pp. 301–306 (1976).
Boeden et al. "Bead Cellulose derivatives . . . ". Journal of Chromatography 552: pp. 389–414 (1991).
Subramanian "Dye–Ligand Affinity Chromatography . . . " CRC Critical Reviews vol. 16, No. 2 p. 169–205 (1984).
Soltz et al. Pharmaceut. Tech. Int. Jun., 1991 pp. 60–65.
Stoltz et al. Biotechnology of Plasma Proteins, Eds. Stoltz & Rivat, Colloque Inserm, 175, pp. 19–24 (1989).
Stoltz et al. Bio–Sciences vol. 6, pp. 103–106 (1987). (just abstract in England).
More & Harvey Blood Separation and Plasma Fractionation, Ed. Harris, Wiley–Liss (1991) pp. 261–306.
Maurel et al. Biotechnology of Plasma Proteins, Eds. Stoltz & Rivat, Colloque Inserm, 175, pp. 31–56 (1989).
Allary et al. Bioseparation, vol. 2, pp. 167–175 (1991).
Taylor et al, Develop. Biol. Standard. vol. 67, pp. 15–24 (1987).
Köppel et al, Clin. Toxicol. Vol. 26, pp. 337–356 (1988).
Feil & Maharaj The Lancet vol. 23, pp. 467–468 (1986).
He & Carter, Nature, vol. 358, pp. 209–215 (1992).
Curling, Methods of Plasma Protein Fractionation, Ed. Curling Academic Press (1980), pp. 77–91.
Berglöf et al., J. App. Biochem., vol. 5, pp. 282–292 (1983): Chromatography.
Anderson et al. J. Chromat. vol. 421, pp. 141–146, (1987).
Ng et al., J. Pharm Sci., vol. 67, pp. 431–433 (1987).
Hao, Vox Sang., vol. 36, pp. 313–320 (1979).
Geisow et al., Techniques in Protein Chemistry, II Ed. Villafranca, Academic Press (1991), pp. 567–573.
Geisow et al., Tibtech. vol. 8, pp. 301–303 (1990).
Polson et al., Prep. Biochem. vol. 13, pp. 137–159 (1983).
Finlayson, Proceedings of the Workshop on Albumin, Bethesda, NIH, pp. 31–45 (1976).
Fürst et al., Beitr. Infusionsther. vol. 24, pp. 83–90 (1989) English translation provided.
Meireles et al., Biotech. & Bioeng., vol. 38, pp. 528–534 (1991).
Grandgeorge & Pelloquin, Transfusion, vol. 29, pp. 629–634 (1989).
Gammelgaard et al., J. Trace Element Electrolytes Health Dis., vol. 3, pp. 39–42 (1989).
Sleep et al., Bio/Technology, vol. 8, pp. 42–46 (1990).
Fleer et al., Bio/Technology, vol. 9, pp. 968–975 (1991).
Latta et al., Biol/Technology, vol. 5, pp. 1309–1314 (1987).
Sijmons et al., Bio/Technology, vol. 8, pp. 217–221 (1990).
Saunders et al., J. Bact., vol. 169, pp. 2917–2925 (1987).
Etcheverry et al., Bio/Technology, vol. 4, pp. 726–730 (1986).

(List continued on next page.)

Primary Examiner—Keith C. Furman

[57] ABSTRACT

A process for the preparation of albumin which has extremely low levels of or is essentially free of colorants, metal ions, human proteins, fragments of albumin, polymers or aggregates of albumin, and viruses, and which is relatively non-glycated, relatively high in free thiol and with an intact C-terminus. The process comprises passing albumin (preferably expressed and secreted by transformed yeast) through two chromatography purifications, ultrafiltering the product, passing through two further chromatography steps and again ultrafiltering the product.

12 Claims, 5 Drawing Sheets

OTHER PUBLICATIONS

Okabayashi et al., J. Biochem., vol. 110, pp. 103–110 (1991).

Sleep et al., Bio/Technology, vol. 9, pp. 183–187 (1991).

Rhodes et al., Meth. Enzymol. vol. 182, (1990) pp. 555–565.

Ringe et al. "A Consumer's Guide to Protein Crystallography", Protein Engineering and Design Paul R. Carey (ed.) (1996) pp. 205–229.

FIG_1

1. OCTANOIC ACID (C8:0)
2. DECANOIC ACID (C10:0)
3. DODECANOIC ACID (C12:0)
4. TETRADECANOIC ACID (C14:0)
5. HEXADECANOIC ACID (C16:0)
6. cis-9-HEXADECANOIC ACID (C16:1)
7. HEPTADECANOIC ACID INTERNAL STD
8. OCTADECANOIC ACID (C18:0)
9. cis-9-OCTADECANOIC ACID (C18:1)
10. cis-9,12-OCTADECANOIC ACID (C18:2)
11. cis-9,12,15-OCTADECANOIC ACID (C18:3)
12. cis-5,8,11,14-EICOSATETRAENOIC ACID (C20:4)

FIG_4
PRIOR ART

1. OCTANOIC ACID (C8:0)
2. DECANOIC ACID (C10:0)
3. DODECANOIC ACID (C12:0)
4. TETRADECANOIC ACID (C14:0)
5. HEXADECANOIC ACID (C16:0)
6. cis-9-HEXADECANOIC ACID (C16:1)
7. HEPTADECANOIC ACID INTERNAL STD
8. OCTADECANOIC ACID (C18:0)
9. cis-9-OCTADECANOIC ACID (C18:1)
10. cis-9,12-OCTADECANOIC ACID (C18:2)

HIGH PURITY ALBUMIN AND METHOD OF PRODUCING

RELATED APPLICATIONS

This application is a continuation-in-part of U.S. patent application Ser. No. 08/265,972, filed Jun. 27, 1994, now abandoned, which is, in turn, a continuation of U.S. patent application Ser. No. 7/949,601 filed Sep. 23, 1992, now abandoned.

The present invention relates to the protein human serum albumin (HSA) extracted from serum and to recombinant human albumin (rHA) produced by transforming a microorganism with a nucleotide coding sequence encoding the amino acid sequence of human serum albumin. In this specification, the term "albumin" refers generically to HSA and/or rHA.

BACKGROUND OF THE INVENTION

Albumin is used to treat patients with severe burns, shock or blood loss. It is also used to supplement media used for growing higher eukaryotic cells. At present, the demand for the product is satisfied by albumin extracted from human blood. Examples of extraction and separation techniques include those disclosed in: JP 03/258 728 on the use of a cation exchanger; EP 428 758 on the use of anion exchange; and EP 452 753 on the use of heating, adding salt and diafiltering.

The production of rHA in microorganisms has been disclosed in EP 330 451 and EP 361 991. Purification techniques for rHA have been disclosed in: WO 92/04367, removal of matrix-derived dye; EP 464 590, removal of yeast-derived colorants; and EP 319 067, alkaline precipitation and subsequent application of the rHA to a lipophilic phase.

SUMMARY OF THE INVENTION

The present invention provides highly purified albumin and processes for obtaining it. The albumin is characterized by extremely low levels of, or by being essentially free of, colorants, lactate, citrate, metals, human proteins such as immunoglobulins, pre-kallikrein activator, transferrin, $\alpha_1$-acid glycoprotein, haemoglobin and blood clotting factors, prokaryotic proteins, fragments of albumin, albumin aggregates or polymers, endotoxin, bilirubin, haem, yeast proteins and viruses. By "essentially free" is meant below detectable levels. The term "colorant" as used herein means any compound which colors albumin. For example, a pigment is a colorant which arises from the organism, especially yeast, which is used to prepare recombinant albumin, whereas a dye is a colorant which arises from chromatographic steps to purify the albumin. At least 99%, preferably at least 99.9%, by weight of the protein in the albumin preparations of the invention is albumin. Such highly pure albumin is less likely to cause adverse side effects.

The albumin of the invention is at least 99.5% monomeric, preferably essentially 100% monomeric, and is characterized by one or more of the following characteristics. It has an aluminum ion content of less than 150 ng, preferably less than 100 ng; an iron ion content of less than 3,000 ng, preferably less than 1,000 ng; a copper ion level of less than 10,000 ng, preferably less than 5,000 ng; a magnesium ion level of less than 3,000 ng, preferably less than 1,500 ng; a zinc ion level of less than 5,000 ng, preferably less than 3,000 ng, a manganese ion level of less than 50 ng, all based on one gram of albumin; a glycation level of less than 0.6, preferably less than 0.15 moles hexose/mole protein; a level of low molecular weight contaminants of below 20 V·sec, preferably less than 10 V·sec as measured in a way defined herein; a single peak on a capillary zone electrophoretogram; an intact, i.e., homogeneous, C-terminus; a free thiol content of at least 0.85 mol SH/mol protein and substantially no C18 or C20 fatty acids.

In accordance with the present invention, highly pure albumin is obtained from an impure albumin solution. The process comprises one or more of the following steps: fermenting a microorganism transformed with a nucleotide sequence encoding the amino acid sequence of human albumin; preferably separating the microorganism cells from the fermentation medium; conditioning the medium, if necessary, for further purification; passing the conditioned medium through two successive chromatography steps; ultrafiltering the product; passing the ultrafiltered product through two further chromatography steps; and ultrafiltering again.

Alternatively, instead of the fermentation medium, the impure albumin solution may be a solution obtained from serum by any of the plethora of extraction and purification techniques developed over the last 50 years, for example those disclosed in Stoltz et al (1991) *Pharmaceut. Tech. Int.* June 1991, 60–65 and More & Harvey (1991) in "Blood Separation and Plasma Fractionation" Ed. Harris, Wiley-Liss, 261–306.

The final product may be formulated to give it added stability. Preferably, the highly pure albumin product of the invention contains at least 100 g, more preferably 1 kg or 10 kg of albumin, which may be split between a plurality of vials.

BRIEF DESCRIPTION OF THE DRAWINGS

The invention is further illustrated in the appended drawings in which.

DETAILED DESCRIPTION OF THE INVENTION

Figure 1:
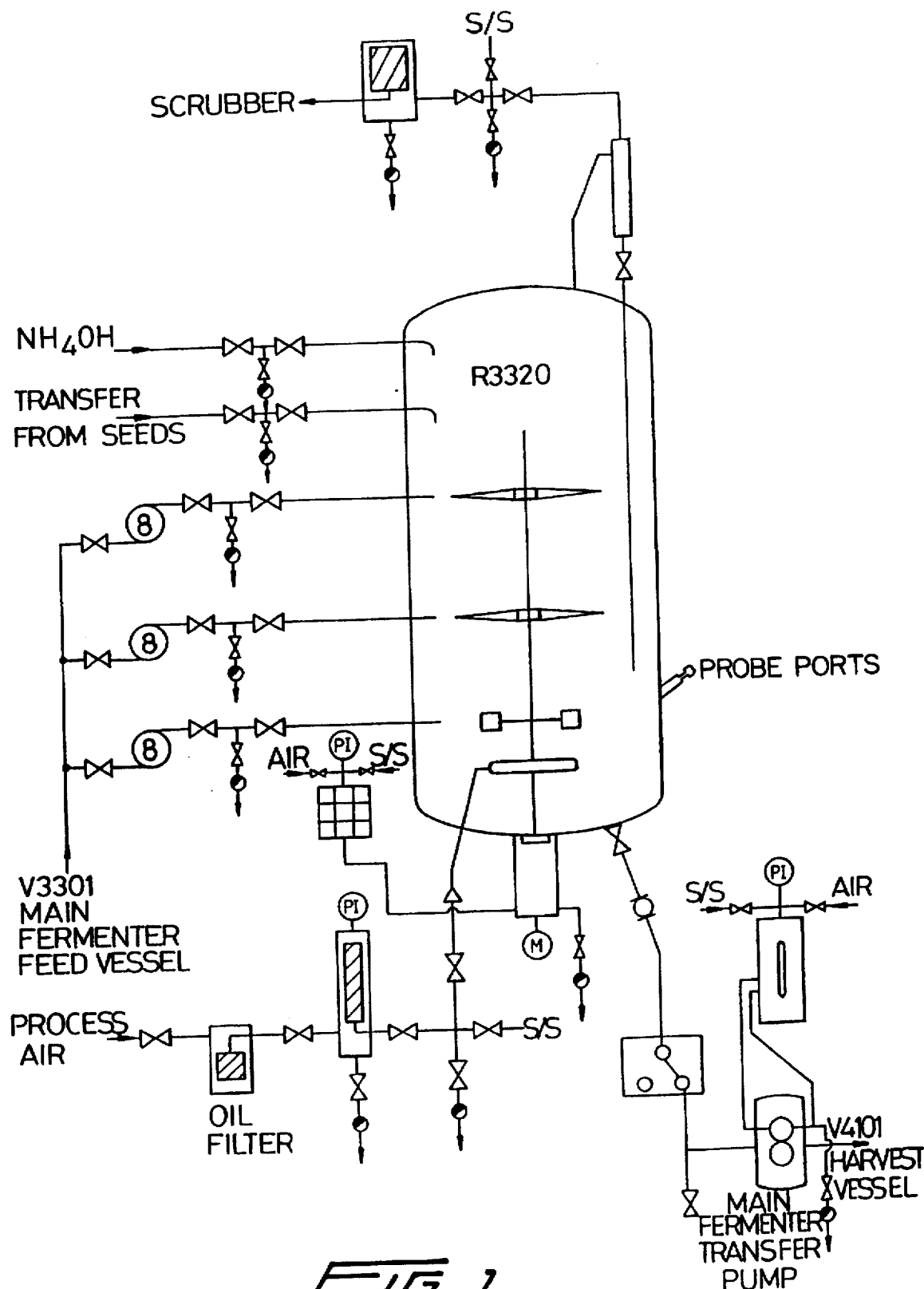
FIG. 1 shows schematically the fermenter used in the main fermentation, described below.

While the process of the present invention can be utilized to obtain highly purified albumin from an impure albumin solution from a number of sources, such as serum, it is particularly applicable to purifying recombinant human albumin (rHA). The albumin produced in accordance with the invention may be any mammalian albumin, such as rat, bovine or ovine albumin, but is preferably human albumin.

It is recognized that DNA encoding albumin may be expressed in a suitable host to produce albumin. Thus, DNA may be used in accordance with known techniques, appropriately modified in view of the teachings contained herein, to construct an expression vector, which is then used to transform an appropriate host cell for the expression and production of albumin. Such techniques include those disclosed in U.S. Pat. Nos. 4,440,859 issued 3 Apr. 1984 to Rutter et al; 4,530,901 issued 23 Jul. 1985 to Weissman; 4,582,800 issued 15 Apr. 1986 to Crowl; 4,677,063 issued 30 Jun. 1987 to Mark et al; 4,678,751 issued 7 Jul. 1987 to Goeddel; 4,704,362 issued 3 Nov. 1987 to Itakura et al; 4,710,463 issued 1 Dec. 1987 to Murray; 4,757,006 issued 12 Jul. 1988 to Toole, Jr. et al; 4,766,075 issued 23 Aug. 1988 to Goeddel et al; and 4,810,648 issued 7 Mar. 1989 to Stalker, all of which are incorporated herein by reference.

The DNA encoding the albumin may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell. Host cells so transformed are then cultured for a sufficient time and under appropriate conditions known to those skilled in the art, and in view of the teachings disclosed herein, to permit the expression of the albumin, which can then be recovered.

Many expression systems are known, including bacteria (for example *E. coli* and *Bacillus subtilis*), yeasts (for example *Saccharomyces cerevisiae*, *Pichia pastoris* and *Kluyveromyces lactis*), filamentous fungi (for example Aspergillus), plant cells, animal cells and insect cells. The preferred microorganism is the yeast *Saccharomyces cerevisiae*.

The vectors include a prokaryotic replicon, such as the ColE1 *ori*, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells. An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers his3, trp1, leu2 and ura3. Plasmids pRS413–416 are Yeast Centromere plasmids (YCps)

A variety of methods have been developed to operatively link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities. Synthetic linkers containing a variety of restriction endonuclease sites are commercially available from a number of sources including International Biotechnologies Inc, New Haven, Conn., USA.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

A desirable way to modify the DNA is to use the polymerase chain reaction as disclosed by Saiki et al (1988) *Science* 239, 487–491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

The yeast is transformed with an expression plasmid based on the *Saccharomyces cerevisiae* 2 μm plasmid. At the time of transforming the yeast, the plasmid contains bacterial replication and selection sequences, which are excised, following transformation, by an internal recombination event in accordance with the teaching of EP 286 424. The plasmid also contains an expression cassette comprising: a yeast promoter (the *Saccharomyces cerevisiae* PRB1 promoter), as taught in EP 431 880; a sequence encoding a secretion leader which comprises most of the natural HSA secretion leader, plus a small portion of the *S. cerevisiae* α-mating factor secretion leader as taught in WO 90/01063; the HSA coding sequence, obtainable by known methods for isolating cDNA corresponding to human genes, and also disclosed in, for example, EP 73 646 and EP 286 424; and a transcription terminator, namely the terminator from Saccharomyces ADH1, as taught in EP 60 057.

The choice of various elements of the plasmid described above is not thought to be directly relevant to the purity of the albumin product obtained, although the elements may contribute to an improved yield of product. A preferred embodiment of the fermentation process is shown in Example 1.

EXAMPLE 1

The cloning strategy for construction of the albumin-producing microorganism was as disclosed in EP 431 880.

Plasmid pAYE316 was introduced into *Saccharomyces cerevisiae* strain D88 (MATa, leu2, [cir°]) by the method described by Hinnen et al, (1978) P.N.A.S. 75, 1929. Transformants were selected on a minimal medium lacking leucine (Yeast nitrogen base, Difco). When transformants were grown for 72 hours at 30° C., 200 rpm in 50 ml flasks containing either 10 ml of complex (YEP, 1% (w/v) yeast extract, 2% (w/v) bactopeptone and 2% (w/v) sucrose), or defined (0.15% (w/v) yeast nitrogen base without amino acids and ammonium sulphate, 0.5% (w/v) ammonium sulphate, 0.1M citric acid/Na$_2$HPO$_4$.12H$_2$O pH6.5, 2% (w/v) sucrose)liquid medium, rHA could be detected in the cell free culture supernatant by SDS-polyacrylamide gel electrophoresis and/or by rocket gel immunoelectrophoresis.

A stock master cell culture and running stocks (manufacturer's working cell bank) of process yeast suitable for the preparation of shake flask cultures were prepared according to the following protocol.

a. An appropriate inoculum was transferred to 100 ml of sterile buffered minimal medium (BMM), shown in Table 1.

TABLE 1

BMM - SALTS MEDIUM

| Constituent | Per Liter |
|---|---|
| Yeast nitrogen base (Difco) (without amino acids, without (NH$_4$)$_2$SO$_4$) | 1.70 g |
| (NH$_4$)$_2$SO$_4$ | 5.00 g |
| Citric acid monohydrate | 6.09 g |
| Na$_2$HPO$_4$, anhydrous | 20.16 g |
| Demineralized water to final volume of | 1 liter |
| Check pH is 6.5 ± 0.2 | |

Sucrose, 2% (w/v), was added as the carbon source. Sucrose must not be heat sterilized together with the other medium components, which may be sterilized by heat or sterile filtration. Sterile filtration is an option for medium sterilization.

b. Incubate the shake flask at 30° C. on an orbital shaker (200 rpm) until the cell density is 1.5-1.7 gL$^{-1}$ (30±6 hrs) as determined by OD$_{600}$ using a standard curve.

c. Mix the culture with 100 ml sterile 40% (w/v) trehalose, a cryoprotectant, before transferring 1 ml aliquots to cryovials, then freezing at or below -70° C.

Running stocks are thus prepared with a vial of the master stocks as the seed for the shake flask in step a. After they have been frozen for at least one week, 3 vials are removed. The recovery of 2 vials is checked by putting each into 100 ml shake flasks containing BMM+2% (w/v) sucrose. The culture should reach a minimum of 1 gL$^{-1}$ at 28 hours. The 3rd vial is used to perform total and viability counts and to check the purity and rHA secretion. Total counts are performed using a Neubauer haemocytometer. Viable counts are carried out on Sabouraud's agar using the Miles and Misra method described in *J. Hygiene* 38, 732-749, (1938). Purity is checked by spreading 100 µl onto each of 2 agar plates containing tryptone soya agar plus cycloheximide. rHA phenotype is determined by plating out about 250 cfu onto an anti-HSA antibody containing plate as described in EP-A-431 880.

Fermentation

This section relates to the production of rHA from stock culture through to the final fermentation and is a general definition of the rHA fermentation process which is not limited to the specific detail of particular equipment or scale. However, detail specific to the growth of the strain D88 [cir°, pAYE316] for the production of rHA has been included.

Shake Flask Culture

Strain D88 [cir°, pAYE316] is grown as an axenic culture physiologically suited for inoculation of the seed vessel. If timing of the seed vessel is to be reproducible, it is necessary to define the phase of growth (primary carbohydrate excess) and inoculum biomass (12±2 mg/L which requires a 100 ml inoculum per 10 liters of medium). The method is as follows:

a. Inoculate one stock vial into a shake flask containing 100 ml of BMM+2% sucrose for each fermentation.

b. Incubate culture at 30° C. on orbital shaker (200 rpm).

c. Allow cell dry weight (cdw) to reach 0.6-1.2 g/L (assessed by OD$_{600}$). Expected time is 24±4 hr for 100 ml BMM.

d. Ensure culture is axenic by microscopic examination.

e. Prepare spread plate (YEPD) of culture for subsequent check of plasmid phenotype for rHA$^+$ (must be >95%).

f. Use this culture to inoculate seed vessel (12±2 mg/L).

Seed Fermentation

This section describes production of an axenic culture of D88 [cir°, pAYE316] by fed-batch fermentation to a high cell dry weight (cdw) of approx. 100 gl$^{-1}$. This culture will provide the inoculum for the production vessel. The feed regime is intended to minimize the accumulation of ethanol and acetate so as to maximize cell yield. The whole of each fermentation is monitored and controlled via the Multi-Fermenter Computer System (MFCS) software available from B. Braun (Germany). The software supplied by B. Braun is a Supervisory Control and Data Acquisition Package. Similar packages are available from other companies. The algorithm is intended to control the addition of sucrose so that maximum biomass is achieved by avoiding the Crabtree effect, i.e. thereby minimizing the production of ethanol and/or acetate. The Feed Control System is based upon the equation:

$$FR=ke^{\mu t}$$

wherein FR is Feed rate, k is the Initial Feed Rate, µ is exponential growth rate, and t is time. The value k has been determined empirically, but is related to the level of biomass in the culture, k has been determined as having the value 0.08 ml of MW10 Feed Medium per minute per liter of culture. The value µ is related to the maximum growth rate of a fully respirative organism. For D88 [cir° pAYE316] it has been determined as 0.1 h$^{-1}$.

't' is the algorithm parameter which is modulated by other variables and by which Feed Rate is controlled. 't' is related to time in that, if no other factor intervenes, it will increase by 1 minute. Therefore without intervention, as t increases linearly with time, FR would increase exponentially with the exponent having the value of 'µ'.

't' is modulated by RQ (Respiratory Quotient), DOT (Dissolved Oxygen Tension) and pH. If RQ>1.2, 't' will be reduced by 20 minutes every 10 minutes. If DOT<15% of air saturation (@1 bar.a) 't' will be reduced by 1 minute every minute. If pH<5.0, 't' is given the value -80 hours which effectively reduces FR to zero.

Furthermore, for the Seed Fermenters which experience a batch phase of growth before feeding, 't' is initially given a very low, i.e. large negative, value which effectively results in an FR value of zero. At the end of the batch phase as the carbon source is exhausted DOT rises rapidly. This is used to force a value of zero onto 't' which results in FR having the value of k. The rate of increase in DOT which triggers the modulation of 't' is 15% of air saturation in 30 minutes. Operations such as calibration of pH, use of dissolved oxygen probes and the like are standard in this art.

The vessels are subjected to a hot NaOH wash and pyrogen-free water (PFW) rinse. Each heat sterilized vessel will contain one volume of sterile MW10, medium (Table 2) batch salts plus trace elements. The medium for rHA production can be ultrafiltered (10,000 Mol. Wt. cut-off) to remove endotoxins.

TABLE 2

MW10 MEDIUM

| Constituents | Batch Medium | Feed Medium |
|---|---|---|
| Salts | | |
| $KH_2PO_4$ | 2.74 g/L | 10.9 g/L |
| $MgSO_4.7H_2O$ | 0.58 g/L | 2.3 g/L |
| $CaCl_2.2H_2O$ | 0.06 g/L | 0.24 g/L |
| $H_3PO_4$ (85% w/w) | 0.88 ml/L | 1.76 ml/L |
| Vitamins | | |
| Ca pantothenate | 20 mg/L | 180 mg/L |
| Nicotinic acid | 33.3 mg/L | 300 mg/L |
| m-Inositol | 20 mg/L | 180 mg/L |
| d-biotin | 0.133 mg/L | 0.8 mg/L |
| Thiamine.HCl | 16 mg/L | 32 mg/L |
| Trace element stock | 10 ml/L | 20 ml/L |
| Sucrose | 0* | 500 g/L |
| Trace Element Stock Constituents | | |
| $ZnSO_4.7H_2O$ | 3 g/L | |
| $FeSO_4.7H_2O$ | 10 g/L | |
| $MnSO_4.4H_2O$ | 3.2 g/L | |
| $CuSO_4.5H_2O$ | 0.079 g/L | |
| $H_3BO_3$ | 1.5 g/L | |
| KI | 0.2 g/L | |
| $Na_2MoO_4.2H_2O$ | 0.5 g/L | |
| $CoCl_2.6H_2O$ | 0.56 g/L | |

The trace elements are added to demineralised water, acidified with 35 ml/L of 98% $H_2SO_4$.
*20 g Sucrose/L is added to the batch medium at the 20 L seed fermenter stage. Any convenient method of sterilization may be used, as may any depyrogenation method, for example, ultrafiltration.
N.B. vitamins are always filter sterilized.

After the medium is added to the vessel, the operating temperature of 30° C. is set, as well as the minimum stirrer speed, typically 400–500 rpm. The initial pH is adjusted with ammonia solution (specific gravity 0.901) using a pH controller set at 5.7±0.2. It is preferable for the initial pH to be near the top of this range to facilitate observation of early metabolism since a decline in pH is the first sign of growth detectable by on-line instruments. 2M $H_2SO_4$ is also used as a pH corrective agent. Sucrose to 20 $gL^{-1}$, MW10 batch vitamins, and Breox FMT30 antifoam to 0.04 $gL^{-1}$ are added to the vessel.

Sterile filtered air is introduced into the vessel at 0.5 v/v/m (i.e. 0.5 liter non-compressed air per liter of medium per minute), the medium is inoculated to 12±2 mg cell dry weight $L^{-1}$ from axenic shake flask culture and the MFCS computer system is initiated. The expected batch phase is 52±8 h. MW10 feed must be connected before the end of the batch phase (volume equal to batch volume).

Features of the MFCS control algorithm:
end of batch phase signalled by dissolved oxygen tension (DOT) increase, of >15% in 30 min.
feed initiated at 0.08 ml per liter batch medium.
feed rate increased according to the formula, $FR=ke^{\mu t}$, by time, as above, wherein FR is feed rate; k is initial feed rate, α is specific growth rate (=0.1 $h^{-1}$ in this case), and t="time".
feed rate (via "time") is reduced in response to DOT<15% and/or respiratory quotient (RQ)>1.2.
The feed is stopped if the pH<5.0 or if the temperature <28° C. or >32° C. This may also be done automatically through the control algorithm. The FR is reduced if the average RQ>1.19 over a 2 h period, or if there is evidence of ethanol or acetate accumulation.

Agitation increased to maintain DOT>20% air saturation. Once the feed is started, the concentration of Breox FMT30 is increased to 0.2 $gL^{-1}$ (calculated on final volume). The feed phase duration is 38±4 hr.

The air flow is increased through the fermentation to maintain the values of oxygen uptake rate (OUR) and carbon dioxide evolution rate (CER), at levels sufficient to provide accurate gas analysis. The air flow rate at the end of fermentation is 1 v/v/m. Daily checks are performed to determine purity of culture and cdw. Appropriate samples are retained. At the end of the feed, the culture is transferred to a production vessel.

Production Fermentation

An axenic culture of D88 [cir°, pAYE316] is produced by fed-batch fermentation to a high cdw (>80 $gL^{-1}$) for the production of extracellular rHA. The production fermenter is inoculated at 0.25–1.00 g·cdw·$L^{-1}$ and feeding is initiated. While it is preferred to initiate feeding within one hour, it can delayed if necessary. Due to the very low values of OUR and CER during the initial part of the feed phase and the consequent errors in their measurement, the automatic control of feed rate using RQ is initially disabled. The feed regime is intended to minimize the accumulation of ethanol and acetate, so as to maximize the cell and product yield.

The fermentation is carried out in the fermenter shown in FIG. 1. The fermenter is designed to give optimum gas dissolution and bulk mixing. The vessels, which are subjected to a hot NaOH wash and PFW rinse, will contain one volume of sterile MW10 (Table 2), batch salts and trace elements. This medium may be sterilized independently of the vessel either by heat or filter sterilization. It has been found in accordance with the present invention that it is advantageous for the fermentation medium, such as MW10, to be free of ethylene diamine tetraacetic acid (EDTA), or a salt thereof, since its presence results in a significantly higher degree of colored contaminants in the albumin produced.

The operating temperature is set at 30° C., and the stirrer speed regulated to be sufficient to maintain a homogeneous solution, typically about 50 rpm. The initial pH is adjusted with ammonia solution (SG 0.901) (controller set to 5.7±0.2). 2M $H_2SO_4$ may be used as a second pH corrective agent. The MW10 batch vitamins are added as is a suitable antifoam, as required, (e.g. Breox FMT30 to 0.125 $gL^{-1}$).

Sterile filtered air is added to the vessel at 0.5 v/v/m initially to maximize sensitivity of exhaust gas analysis, and the MFCS computer system is initiated. The vessel is inoculated with whole of seed vessel culture (minimum 0.4% v/v). MW10 feed in a volume equal to the batch volume. The feed is started and the RQ override control disabled until OUR and CER values are sufficiently high to make control effective. The feed rate is adjusted manually during the period without RQ control if RQ is consistently >1.2.

Features of the control algorithm: the feed is initiated at 0.005 ml per min per L batch medium and increased according to the formula, $FR=ke^{\mu t}$, by time, wherein FR is feed rate, k is the initial feed rate, μ is specific growth rate (0.1 $h^{-1}$ in this case) and t is "time". The feed rate (via "time") is reduced in response to DOT<15% and/or RQ>1.2. The feed rate is stopped if pH<5.0, or if the temperature <28° C. or >32° C. This may also be done via the control algorithm.

The feed rate is reduced if the average RQ>1.19 over a 2 h period, or if there is evidence of ethanol or acetate accumulation. Agitation is increased to maintain DOT>20% air saturation. The concentration of Breox FMT30 is increased to 0.2–0.32 gL$^{-1}$ once the culture is under RQ control. The duration of the feed phase (72±5 hr) is dependent upon OTR of the vessel. The vessel is overpressured as necessary to enhance OTR. The air-flow is increased in steps, ensuring that the values of OUR and CER are sufficient to provide accurate exhaust gas analysis. Final air flow should provide 1 v/v/m when the fermenter is full to capacity. Daily checks are performed to determine the purity of culture and cdw. Appropriate samples are retained. The culture is held for downstream processing at the end of the feed.

Hold of Production Culture

The production culture of D88 [cir°, pAYE316] may be held under appropriate conditions to enable batch processing of the culture. The hold time should be kept to a minimum, but can be extended up to 48 hours and beyond if necessary. It will be appreciated that, under conditions of batch processing, the constraints of hold time as expressed herein apply to the final portion of the culture to be processed.

During the hold phase, the temperature of the culture is reduced to the minimum possible, typically between 4° and 15° C., preferably 4° C., and the DOT is allowed to fall to 0%. The feed is stopped, the aeration turned off and the overpressure reduced. The pH control, however, is maintained. Sufficient agitation is maintained to retain the cells in suspension and facilitate cooling and pH homogeneity, preferably about 50 rpm.

rHA Productivity

To determine rHA titer, account must be taken of the contribution made by the cell volume to the productivity of an extracellular protein. Samples for assay can be obtained by either:

(i) diluting the culture until the contribution made by the cells to the volume is not significant (typically 1 in 10 for a high cell density culture). The rHA content of the diluted supernatant (termed whole culture) is then determined by SDS-PAGE; or (ii) centrifuging the culture directly and thereafter determining the supernatant by SDS-PAGE.

The total rHA in fermenter may be determined by either of two calculations:

a) Assume the cell volume is 3 ml/g dry weight (based on published values). The yield (Y) as total mass of albumin is calculated by Y=

$$tV(1 - 3x) 1000$$

where t=titre (g/L by SDS-PAGE supernatant), V is culture volume and x is cell dry weight (g/L), or b) Determine volume fraction of cell pellet after centrifugation and assume the trapped liquid in pellet to be 30% (as for close-packed spheres)

$$Y = tV\left(1 - \frac{0.3 V_p}{V}\right)$$

where t and V are as defined above and Vp is the volume of the cell pellet.

Methods (ii)(a) and (ii)(b) produce very similar results. It is preferable to use either method (i) with either method (ii)(a) or (ii)(b) and attempt to reconcile any differences rather than using a single method.

The expected yields in accordance with the above procedure are: Biomass>80 g cell dry weight/L culture; rHA>1.5 g/L culture (SDS-PAGE—whole culture).

In order to prepare an impure albumin solution for purification treatment in accordance with the present invention when the albumin is rHA, the microorganism cells are removed from the fermentation culture medium. While it is preferred that the cells be removed prior to beginning of the purification process as described, it can be carried out simultaneously with the first step under certain conditions, e.g. where the first purification step is carried out in a fluidized bed. The fermentation culture, which has been cooled in the fermenter during the hold phase to less than 15° C. without aeration, is transferred to a tank where it is diluted to give a biomass concentration of 180–210 g/kg and cooled further if necessary. The diluted culture should be held for as short a time as possible without aeration at reduced temperature with sufficient agitation to prevent yeast cell deposition.

Cells and supernatant are subjected to a primary separation step, for example microfiltration or centrifugation in any appropriate centrifuge such as an Alfa Laval BTUX510 continuous discharge nozzle run at 5700 rpm. Centrate so produced may be filtered in line, for example using a depth filter, 1 μm, supplied by Cuno, to remove residual whole and broken yeast cells and other particles. At least 75% of the rHA present in the diluted culture is recovered in a single pass centrifugation operation. The resultant solution is then treated by the process of the invention to purify the albumin contained therein as shown in Example 2.

EXAMPLE 2

The centrate from a fermentation, such as described in Example 1, is prepared, or conditioned, for chromatography on a cation exchange matrix while protecting the rHA from polymerization and protease activity. Preferably, sodium octanoate is added (Chromatography Recipe 13—Table 3) to a final concentration of approximately 5 mM. The pH is adjusted with acetic acid (Chromatography Recipe 9) to 4.50±0.1 (preferably ±0.05) and the conductivity is checked to be <5.5 mS cm$^{-1}$.

Chromatography

All operations may be carried out at ambient temperature (20°±5° C.). The direction of the linear flow refers to flow either down the column (D) or up the column (U). The step end point defines the circumstances under which a step is ended. This occurs when the predetermined volume is reached or before if one of three monitor signals passes up (U) or down (D) through the predetermined value. The step end point volume refers to column volumes. The $A_{280}$ value is quoted in absorbance units/cm length of pathcell. The rHA loads (g rHA/L matrix) for the chromatography columns are determined from titers of rHA (g/L) by either SDS-PAGE (in the case of the S-FF column) or GP-HPLC (for all other columns).

Cation Exchange Chromatography rHA is concentrated and purified with respect to at least yeast antigens, low molecular weight contaminants and pigment by the commercial cation exchange matrix S-Sepharose FF (Pharmacia) at a bed height of 12.5 cm, with a column loading of 40±10 g rHA/L matrix. The conditioned centrate is loaded on the column and the rHA is purified using the following conditions (Table 4). Other suitable cation exchange resins include SP-Sepharose FF, SP-Spherosil, CM-Sepharose FF, CM-Cellulose, SE-Cellulose and S-Spherodex.

TABLE 3

CHROMATOGRAPHY RECIPES FOR THE ROUTINE PURIFICATION OF rHA

| Solution | | Concentration | | Conductivity |
|---|---|---|---|---|
| No | Name | Constituent | (gL$^{-1}$) / pH | (mS cm$^{-1}$) |
| 1 | S-FF Equilibrant/Wash | CH$_3$OONa.3H$_2$O / CH$_3$COOH (glacial) | 3.69 / 0.220 — pH 5.45–5.65 | 1.9–2.2 |
| 2 | S-FF Eluent | CH$_3$COONa.3H$_2$O / CH$_3$COOH (glacial) | 13.6 / 0.750 — pH 5.45–5.65 | 6.5–7.5 |
| 3 | DBA Eluent | NaCl / CH$_3$COONH$_4$ / NaOH | 117 / 3.84 / 0.680 — pH 9.0–9.4 | 125–165 |
| 4 | 0.5M Sodium Hydroxide | NaOH | 20.0 — pH >12 | 80–120 |
| 5 | Gel Permeation | CH$_3$COONa.3H$_2$O / CH$_3$COOH (glacial) / Octanoic Acid / NaOH | 4.94 / 0.380 / 0.721 / 0.190 — pH 5.4–5.6 | 2.9–3.3 |
| 6 | DE-FF Eluent | Na$_2$B$_4$O$_7$.10H$_2$O / NaCl | 7.62 / 5.84 — pH 8.9–9.3 | 11.7–13.5 |
| 7 | 20 mM Sodium Hydroxide | NaOH | 0.800 — pH >12 | 3.5–5.5 |
| 8 | DE-FF Equilibrant | CH$_3$COONa.3H$_2$O / CH$_3$COOH (glacial) / Octanoic Acid / NaOH | 4.94 / 0.380 / 0.721 / 0.190 — pH 5.4–5.6 | 2.9–3.3 |
| 9 | Acetic Acid | CH$_3$COOH | Glacial | — |
| 10 | DE-FF Wash | Na$_2$B$_4$O$_7$.10H$_2$O | 7.62 — pH 9.0–9.4 | 2.3–2.9 |
| 11 | DE-FF Pre-equilibrant | CH$_3$COONa.3H$_2$O / CH$_3$COOH (glacial) | 61.8 / 2.98 — pH 5.5–5.7 | 24–28 |
| 12 | DBA Equilibrant/Wash | NaCl / CH$_3$COONH$_4$ / NaOH | 11.7 / 0.960 / 0.150 — pH 8.8–9.2 | 18–22 |
| 13 | 2M Sodium Octanoate | Octanoic Acid / NaOH | 288 / 76.0 — pH 7.7–8.2 | — |
| 14 | 1.73M Phosphoric acid | H$_3$PO$_4$ (85% (w/w)) | 200 — pH <1.2 | — |
| 15 | 2M Ammonia | NH$_4$OH (30% NH$_3$ (w/w)) | 113 ml | — |

All weighings are ± 2%, for this particular example. Generally, the concentrations may be varied by ± 25%, preferably only ±20%, 15%, 10% or 5%.

TABLE 4

| | | Linear Flow | | Step End Point | | | |
|---|---|---|---|---|---|---|---|
| | | | | | Override | | |
| S-FF Step | Recipe No. | Rate (cm/min) | Direction | Vol | pH | mS/cm | A$_{280}$/cm |
| 1. Equilibration | 1 | 6.36 | D | 4 | 6(D) | — | — |
| 2. Load | — | 6.36 | D | — | — | — | — |
| 3. Wash | 1 | 6.36 | D | 11.5 | — | — | 0.4(D) |
| 4. Elution | 2 | 3.18 | D | 2 | — | — | 1.0(U) |
| 5. Eluate Collection | 2 | 3.18 | D | 6.5 | — | — | 0.6(D) |
| 6. Salt wash | 3 | 3.18 | D | 3.5 | — | — | 0.8(D) |
| 7. NaOH wash | 4 | 3.18 | D | 3 | — | — | — |
| 8. Storage 1 | 7 | 3.18 | D | 3 | — | 12(D) | — |
| 9. Storage 2 | 7 | 3.18 | D | 0.5 | — | — | — |
| 10. pH Adjustment | 15 | Adjust pH of eluate to 9.0 ± 0.2 with Ammonia | | | | | |

Recovery of rHA >40% (Centrate SDS-PAGE, S-eluate HPLC)

Affinity Chromatography

This step further purifies the rHA with respect to a 45 kD N-terminal albumin fragment, yeast antigens and pigment. The affinity matrix may comprise any Cibacron Blue type of dye which binds albumin, for example Reactive Blue 2, Procion Blue HB, Blue Sepharose, Blue Trisacryl and other anthraquinone-type compounds. Preferably, the matrix is the "Delta Blue" Matrix, prepared as described hereinafter utilizing the following materials.

1,4 Diaminobutane—minimum purity of 98%, used as the free base. This is a very hygroscopic material which is generally stored frozen and dispensed by weight.

Reactive Blue 2—having the chemical structure represented below.

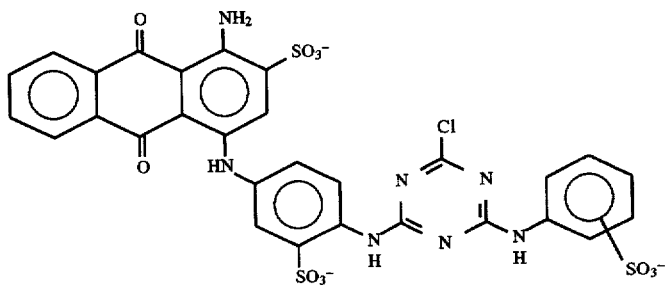

Theoretically, the preferred isomer is the ortho-$SO_3$ form, but as it is difficult to make, the meta isomer is preferred. The objective of the following process is to prepare aminobutyl-Reactive Blue 2 with a minimum purity of 98% total peak area as determined by analytical HPLC. This can be achieved either by using crude commercially available dye which will necessitate purification of the aminobutyl derivative dye or using a pure synthesised dye. In the latter method, the starting dye material should be a minimum of 98% pure by analytical HPLC at 280 nm. Such material is available from ACL, Isle of Man. The actual content of the dye or dye/spacer sample to be used is determined by standard addition using a dye standard to a solution containing a known weight of the sample.

Process Water is of the quality of de-ionised or reverse osmosis water and can be filter sterilized. All solutions prepared from process water and used in the production of Delta Blue Agarose are filtered through a Pall 0.22 µm filter.

Process for the Production of Aminobutyl-Reactive Blue 2

Reactive Blue 2 (weight equivalent to 500 g=0.6 mol by the standard addition method) is dissolved in water (12L) and added slowly with stirring to a solution of 1,4-diaminobutane (880 g) in water (2L). The mixture is then heated to 60° C. and held at this temperature for 2 hours after which sodium chloride (700 g) is added and the reaction allowed to cool whilst stirring. The derivatised dye is then completely precipitated from solution by the addition of sufficient concentrated hydrochloric acid. Precipitation from solution can be judged by spotting the solution on a filter paper, a clear wet non-blue ring surrounding the precipitate being indicative of complete precipitation.

The precipitate is collected by filtration and washed with 0.5M hydrochloric acid (20L), then re-dissolved in water (16L). Sodium hydroxide can be added to enable dissolution of the precipitate. The aminobutyl dye is re-precipitated by addition of sodium chloride (1600 g) followed by sufficient concentrated hydrochloric acid to complete precipitation. The precipitate is collected by filtration, pressed to remove excess liquors and then re-dissolved in the minimum required volume of water. The pH of the resulting solution is adjusted to pH12 using sodium hydroxide.

Final Product Specification

The purity of aminobutyl-Reactive Blue 2 should be at least 98% total peak area by analytical HPLC at 280 nm and a single band by t.l.c. with no baseline retentate. The final product should be shown to be free of diaminobutane and any residual materials present should be shown to be non-reactive. Analytical Methods—Analytical HPLC. Column= $C_{18}$ reverse phase, 5 µm particle size, 4.7×100 mm (Whatman or equivalent); flow rate—1 ml/min total; solvent A=water, B=95% (v/v) methanol/water containing 0.1% (w/v) cetyltrimethylammonium bromide; wavelength=280 nm;

| | |
|---|---|
| 0 | 85 |
| 2 | 85 |
| 8 | 90 |
| 10 | 100 |
| 35 | 100 |

Standard Addition Assay

The absorbance at 620 nm of a dye containing solution is determined ($A_{620}$). This absorbance should be in the range 0.1–0.5. 10 µl of a dye standard of known concentration in the range 2–4 mM is added to 1 ml of the solution and the increase in absorbance ($\Delta A_{620}$) measured. The dye concentration in the sample may then be calculated from:

$$\text{Sample conc.} = \frac{A_{620} \times \text{Standard conc.}}{\Delta A_{620} \times 101}$$

Thin Layer Chromatography

Analysis of samples by t.l.c. is carried out using Silica G plates with a propan-2-ol:ammonia:water (7:2:1) solvent. Load levels of 5–10 µg should be run and no material should remain on the baseline. The plate is dried thoroughly, sprayed with ninhydrin reagent (e.g. BDH) and heated to approximately 110° C. to test for amino compounds, e.g. 1,4-diaminobutane.

Epichlorohydrin Activation of Sepharose CL-6B

Raw Material Specification

The matrix to be derivatized is an agarose-based matrix such as Sepharose CL-6B (Pharmacia, Sweden) or equivalent. A pressure flow curve should be determined for the Sepharose CL-6B and no visible sign of bead damage should be detectable by microscopic analysis of the beads. The epichlorohydrin (1-chloro-2,3-epoxypropane) should be of a minimum purity of 98% by g.l.c. as determined by the manufacturer.

Process Note

Weights of Sepharose CL-6B gel are wet weight of gel allowed to drain free of excess water under gravity on a sintered filter. Sepharose CL-6B is washed with water to remove ethanol and allowed to drain free of excess water. The wash volume required will depend on the wash method used, but washing should achieve >99.9% removal of ethanol. The gel (1 kg) is then transferred to a reaction vessel containing 0.7M sodium hydroxide (1000 ml). The slurry is stirred vigorously during the addition of epichlorohydrin (80 ml). The stirring can then be reduced during the remainder of the reaction which is carried out at 20° C.±5° C. for 16 h. Upon completion of the reaction, the gel is washed with water to remove epichlorohydrin and allowed to drain free of excess water. At the end of washing, a 5 ml sample of wash added to the epoxide group assay in place of the gel should cause no increase in pH.

Final Product Specification

The epichlorohydrin activated Sepharose CL-6B should have an epoxide content of 630±40 μmole/g dry weight as determined by the epoxide group titration method (see below). The activated Sepharose CL-6B should be capable of preparing Delta Blue Agarose containing 50±5 μmole dye/g dry weight as detailed in Delta Blue Agarose Production (see below) and analyzed by the analytical method for Dye Substitution Level (see below). No sign of bead damage should be detectable by microscopic examination of the beads.

Analytical Methods

Pressure Flow Curve Determination

This determination requires a pump (0–100 ml/min at up to 1.5 bar), a bubble trap with pressure gauge (0–1.5 bar) and a 32 mm diameter (8.0 cm$^2$ cross sectional area)×250 mm adjustable column.

Water washed matrix is drained to a packed bed under gravity. 125 g of this matrix is suspended in 0.1M NaCl (75 ml) and packed into the column under gravity. When the bed has packed, the end adapter is inserted and 0.1M NaCl (150 ml) passed through the column at 5 ml/min. The pressure, flow rate and bed height are then measured.

The flow rate is increased and the system left until bed height and pressure have stabilized. The new values of pressure, flow rate and bed height are determined. This process is repeated until either 100 ml/min or 1.5 bar is reached.

An experiment with no matrix should also be performed to determine the pressure drop due to the system itself at various flow rates. These values of pressure drop should be subtracted from those determined with the matrix to ascertain the pressure drop due to the matrix itself. These values should be plotted against the measured flow rate to give the requisite pressure flow curve.

Epoxide Group Titration

To determine accurately the epoxide group content of the activated gel, samples of water-washed and drained gel are taken simultaneously for dry weight determination and epoxide titration. The dry weight can be determined by drying a known weight (approximately 1 g) of wet gel in a centrifugal vacuum evaporator or heated vacuum oven at 60° C. to constant weight.

The epoxide titration is based upon the method described by Sundberg and Porath in the *J. Chromatography* 90, 87–98 (1974). To a known weight of wet gel (3–5 g) is added 1.3M sodium thiosulphate (15 ml). The released sodium hydroxide is continuously titrated using 0.02M volumetric standard hydrochloric acid so as to keep the pH close to neutrality until the reaction is complete. The end point of the reaction is reached when the rate of change of pH is equal to or less than 0.12 pH unit per minute at pH7. The results are expressed as μmole/g dry weight gel, assuming 1 mol hydroxide released per mol epoxide.

Delta Blue Agarose Production

A solution of pure aminobutyl-Reactive Blue 2 (weight equivalent to 2.5 g=2.75 mmol by the standard addition method) in water (1000 ml) is prepared by diluting the stock solution and adjusting with sodium hydroxide to pH 12 if necessary. Epoxy-activated Sepharose CL-6B (1 kg) is added to the aminobutyl-Reactive Blue 2 solution with stirring and the reaction allowed to proceed for 16 h at 20° C. When the reaction is complete, the gel is washed free of excess dye using water until the absorbance at 620 nm of the washings is equal to or less than 0.010AU. The gel is then allowed to drain free of excess liquid by gravity, then a sample is taken and assayed for excess epoxide groups.

For blocking excess epoxide groups, the gel (1 kg) is suspended in 50 mM NaOH (1000 ml) and 50 ml of 2-mercaptoethanol (minimum purity of 99% by g.l.c.) added thereto. The slurry is stirred for 16 h at 20° C., washed free of excess 2-mercaptoethanol using water and then drained free of excess water. A sample of gel is removed for epoxide group titration. If any are detectable, the above blocking procedure should be repeated and then the gel re-analyzed.

When the gel is completely blocked, it is washed with 30% (v/v) ethanol containing 0.5M NaOH, until the $A_{620}$ of the washing is equal to or less than 0.005AU. The gel is then washed with 20 mM sodium hydroxide and stored/transported in this solution. The dye content of the gel is determined in the final product as detailed below, the breakthrough, recovery, capacity for HSA determined as below and a pressure flow curve determined as above.

Final Product Specification

The final product (Delta Blue Agarose) should have a dye content of 50±5 μmole/g dry weight. No sign of bead damage should be detectable by microscopic examination of the beads. The final product should have an HSA capacity of not less than 20 mg/ml bed volume at 5% breakthrough.

Analytical Methods—Dye Substitution Level

Samples of water-washed and drained gel are taken simultaneously for dry weight and immobilised dye determination. For the latter, a known weight (approximately 0.3 g) is hydrolysed in 5M hydrochloric acid (6 ml) at 60° C. for 10 min or until optically clear. The solution is then cooled on ice and 10M sodium hydroxide (3 ml) added, followed by 1M sodium phosphate pH 7 (21 ml). Dye content of the hydrolysate is determined by standard addition. The substitution level is expressed as μmole dye/g dry weight of gel.

Delta Blue Agarose (DBA) Performance Testing

Column=Diameter 1.4 cm, 5 ml bed volume of Delta Blue Agarose; Buffer 1=Equilibration, 110 mM sodium acetate pH 5.5; Flow rate=1 ml min$^{-1}$; Temperature=20°–25° C.: Load sample=Sigma HSA (Cat. No. A8763)–3 mg/ml in buffer 1.

For capacity determination, 1 ml fractions are collected immediately upon sample loading and the absorbance at 280 nm of each fraction determined. These figures are plotted against mg HSA loaded and the breakthrough point at which $A_{280}$ is 5% of sample $A_{280}$ is determined. This capacity is expressed as mg HSA/ml bed volume.

Use of Blue Matrix

The method uses DBA at a bed height of 25 cm, with a column loading of 10±1 g rHA/L matrix. The pH-adjusted S-FF eluate is loaded on the column and the rHA is purified using the conditions shown in Table 5.

Intermediate Ultrafiltration

This step concentrates the rHA for loading onto Sephacryl S-200 HR. A cellulose-type membrane, nominal molecular weight cut off 10,000, in an ultrafiltration apparatus is used to concentrate DBA eluate to a retentate concentration of 80–110 g rHA/L. The membranes are treated, post-use, by flushing out residual protein with water, or solutions 3 or 5 from Table 3, and cleaning with 0.1M sodium hydroxide. The membranes may then be stored in 20 mM sodium hydroxide. Recovery of rHA>90% (HPLC).

Gel Permeation Chromatography

This step purifies the rHA with respect to yeast antigens, pigment and dimerized albumin and performs a buffer exchange step. The method uses a commercial gel permeation matrix such as Sephadex G100, G150, G250, Sephacryl S-100, S-200 or S-300, TOYOPEARL HW50S or Superose 6 or 12. Preferably, the matrix is Sephacryl S-200 HR (Pharmacia) at a bed height of 90 cm (3×30 cm). The retentate from intermediate ultrafiltration is loaded onto the column. Recycle and product fractions are collected. This step is repeated until all the material has been loaded onto the column. The process is diagrammed in Table 6.

TABLE 5

| DBA Step | Recipe No. | Linear Flow Rate (cm/min) | Direction | Vol | pH | Step End Point Override mS/cm | $A_{280}$/cm |
|---|---|---|---|---|---|---|---|
| 1. Equilibration | 12 | 1.53 | D | 7 | 9.5 (D) | — | — |
| 2. Load | — | 1.53 | D | — | — | — | — |
| 3. Wash | 12 | 1.53 | D | 5 | — | — | — |
| 4. Elution | 3 | 1.53 | D | 2 | — | — | 0.4(U) |
| 5. Eluate Collection | 3 | 1.53 | D | 3 | — | — | 0.4(D) |
| 6. NaOH wash | 4 | 1.53 | U | 2 | — | — | — |
| 7. Storage 1 | 7 | 1.53 | U | 2 | — | 12(D) | — |
| 8. Storage 2 | 7 | 1.53 | U | 0.5 | — | — | — |

TABLE 6

Purification of Intermediate Ultrafiltration Retentate

| S-200 HR Step | Recipe No. | Linear Flow Rate (cm/min) | Direction | Vol | pH | Step End Point Override mS/cm | $A_{280}$/cm | Action |
|---|---|---|---|---|---|---|---|---|
| 1. Equilibration | 5 | 0.75 | D | 3.23 | 7(D) | — | — | |
| 2. Load | — | 0.75 | D | 0.075 | — | — | — | |
| 3. Elution | 5 | 0.75 | D | 1.0 | — | — | 10%(U) max. | Start recycle collec. |
| | | | | | | | 90%U max. | End recycle collec. Start product collec. |
| | | | | | | | 0.5 | End product collec. |
| 4. Loop to step 2 | — | — | — | — | End of Load Material | | | |
| 5. Eluent wash | 5 | 0.75 | D | 0.50 | — | — | — | |

S-200 HR Recycle Ultrafiltration

A cellulosic type membrane, nominal molecular weight cut-off 10,000, in an ultrafiltration apparatus, is used to concentrate the pooled recycle fraction to a retentate concentration of 80–110 g rHA/L. The membranes are treated, post-use as described above under Intermediate Ultrafiltration.

Alternatively, as in any ultrafiltration steps in this process, polysulfone membranes with a cut-off of $\leq 30,000$ may be used instead of the cellulose-type membranes. Such membranes are available from Amicon and Millipore. Membranes used in depyrogenation should have a cut-off of $\leq 10,000$.

Purification of S-200 HR Recycle Ultrafiltration Retentate

The retentate from recycle ultrafiltration is loaded onto the same column as in step (a) and a product fraction collected from each peak. This step is repeated until all the material has been loaded onto the column as diagrammed in Table 7.

Anion Exchange Chromatography

The aim of this step is to purify rHA with respect to at least yeast antigens and pigmented albumin. The method uses an anion exchange matrix such as QMA-Spherosil, DEAE-Spherodex, Q-Hyper D, DEAE-cellulose, QAE-cellulose, or TMAE, DMAE, or DEAE FRACTOGEL. Preferably, the matrix is the commercial anion exchange matrix DE Sepharoseo-FF (Pharmacia) at any convenient bed height, such as 12.5 cm, with a column loading of 35±15 g rHA/L matrix. The rHA in diluted S-200 eluate is loaded on the column and purified using the conditions diagrammed in Table 8.

TABLE 7

Purification of S-200 HR Recycle Ultrafiltration Retentate

| S-200 HR Step | Recipe No. | Linear Flow Rate (cm/min) | Direction | Vol | pH | Step End Point Override mS/cm | $A_{280}$/cm | Action |
|---|---|---|---|---|---|---|---|---|
| 1. Equilibration | 5 | 0.75 | D | 0.10 | — | — | — | |
| 2. Load | — | 0.75 | D | 0.075 | — | — | — | |
| 3. Elution | 5 | 0.75 | D | 1.00 | — | — | 90% (U) max. | Start product collec. |
| | | | | | | | 0.5 | End product collec. |
| 4. Loop to step 2 | — | — | — | — | End of Load Material | | | |

TABLE 7-continued

Purification of S-200 HR Recycle Ultrafiltration Retentate

| S-200 HR Step | Recipe No. | Linear Flow Rate (cm/min) | Direction | Vol | Step End Point pH | Override mS cm | $A_{280}$/cm | Action |
|---|---|---|---|---|---|---|---|---|
| 5. NaOH wash | 4 | 0.375 | U | 0.25 | — | — | — | |
| 6. Storage 1 | 7 | 0.375 | U | 2.0 | — | 6 (D) | — | |
| 7. Storage 2 | 7 | 0.375 | U | 0.15 | — | — | — | |
| 8. Dilution | | Dilute product to 10 g rHA/L or to a convenient volume with DE-FF equilibration buffer (Recipe 8). | | | | | | |

Recovery of rHA >65% (HPLC) per cycle
The product fractions are pooled.

TABLE 8

| DE-FF Step | Recipe No. | Linear Flow Rate (cm/min) | Direction | Vol | Step End Point pH | Override mS cm | $A_{280}$/cm |
|---|---|---|---|---|---|---|---|
| 1. Pre-equilibration | 11 | 4.4 | D | 20 | 6(D) | — | — |
| 2. Equilibration | 8 | 4.4 | D | 10 | — | — | — |
| 3. Load | — | 3.1 | D | — | — | — | — |
| 4. Wash | 10 | 3.1 | D | 10 | 9(U) | — | — |
| 5. Elution | 6 | 3.1 | D | 5 | — | — | 0.4(U) |
| 6. Eluate Collection | | | | 7.5 | | | 0.4(U) |
| 7. Salt wash | 3 | 3.1 | U | 3 | — | — | 0.8(U) |
| 8. NaOH wash | 4 | 3.1 | U | 4 | — | — | — |
| 9. Storage 1 | 7 | 3.1 | U | 4 | — | 12(D) | — |
| 10. Storage 2 | 7 | 3.1 | U | 0.25 | — | — | — |
| 11. pH Adjustment | 14 | Adjust pH of eluate to 7.0 ± 0.3 with phosphoric acid | | | | | |

Recovery of rHA >65% (HPLC).
A higher linear flow rate of up to about 6.36 cm · min$^{-1}$ can be used instead. The eluate from the DE-FF column has less than 0.1% (w/w) albumin dimer and an undetectable level of albumin polymers or aggregates.

EXAMPLE 3

This Example illustrates the concentration, diafiltration and formulation of the highly purified rHA into a suitable product, in this instance containing 25% (w/v) albumin. This procedure is carried out in two stages—final ultrafiltration (UF) and Formulation. Final UF begins with transfer of the pH-adjusted DEAE eluate to the Final UF feed vessel and terminates after retentate and washings, if any, are transferred to the formulation vessel. The rHA-containing process stream is sequentially subjected to primary concentration, diafiltration and secondary concentration phases in an ultrafiltration system fitted with cellulosic membranes with a nominal molecular weight cut off limit of 10,000. The initial concentration step increases the rHA concentration to approximately 100 g·L$^{-1}$ and is immediately followed by the continuous diafiltration phase where the albumin is diafiltered against at least 5, preferably at least 7 retentate volume equivalents of water-for-injection. Following diafiltration, the secondary concentration phase further increases the rHA concentration to 275–325 g·L$^{-1}$. At the end of UF the retentate is transferred to the bulk product formulation vessel.

The formulation step produces rHA in an appropriate chemical environment and at an appropriate concentration suitable for bulk product sterile filtration and filling. The transferred Final UF retentate is analyzed to determine concentrations of albumin, sodium and octanoate. These quantities are taken into account and any necessary further amounts of stock sodium chloride and sodium octanoate excipient solutions and appropriate grade water added to achieve the bulk formulation specification. The final albumin concentration may be 235–265 g·L$^{-1}$, with a sodium concentration of 130–160 mM. Any other feasible albumin concentration may be made, however, with a minimum concentration of at least 4% (w/v), preferably 4–25% (w/v). Formulation is complete following addition of appropriate conventional pharmaceutically acceptable excipients and diluting water, such as those specified in the U.S. Pharmacopeia for human albumin.

A final concentration of 0.08 mmoles sodium octanoate per gram of albumin may be desirable. The product is sterile and non-pyrogenic. There is about 1% dimeric albumin but no larger polymers or aggregates are detectable.

EXAMPLE 4

This Example illustrates the analysis that is carried out to establish the purity of albumin purified in accordance with the present invention. Unless stated otherwise, all of the assays are performed on albumin which has been formulated as described in Example 3 to yield the final product.

Glycation of rHA

A microassay for glycated protein has shown that (rHA) purified in accordance with the invention is not modified by non-enzymic glycosylation (glycation). The microassay measures the stable Amadori product (AP) form of glycated protein, by oxidation of the C-1 hydroxyl groups of AP with periodate. The formaldehyde released by periodate oxidation is quantitated by conversion to a chromophore, diacetyldihydrolutidine (DDL), by reaction with acetylacetone in ammonia. DDL is then detected colorimetrically at 405 nm.

| Albumin batch | Mole hexose/mole protein |
|---|---|
| A | 0.092 |
| B | 0.116 |
| C | 0.090 |
| D | 0.132 |
| E | 0.060 |
| G | 0.04 |
| H | 0.01 |
| I | 0.07 |
| J | 0.07 |
| K | 0.05 |
| L | 0.740 |
| M | 0.70 |
| N | 0.96 |
| O | 0.78 |

Batches A-K were rHA purified according to the invention. Batches L-O were samples of commercially available human serum albumin from differing sources.

Low Molecular Weight Contaminant Assay

Rationale

The aim of this assay is to remove non-covalently bound low molecular weight contaminants (LMC) from rHA and HSA using acidic organic solvents. An HPLC "fingerprint" chromatogram can then be produced for comparison of samples.

Method

To 100 μl of final product (20 mg; rHA or HSA) is added sequentially 50 μl formic acid (98% v/v), 100 μl chloroform and 50 μl ethanol with vortexing after each addition. The samples are kept at room temperature for 5 mins with regular mixing. Protein is then precipitated by the addition of 1 ml acetone (30 mins, -20° C.). The protein samples are pelleted by centrifugation and the supernatants are decanted off and dried by rotary evaporation under vacuum. The dried samples are resuspended in 25% acetonitrile/0.1% trifluoroacetic acid. LMCs are then separated on an ABI PTH C18 reverse phase column (220×2.1 mm) using a linear 10%–90% acetonitrile gradient in 0.1% trifluoroacetic acid (flow rate=300 μl/min). The samples were monitored 214 nm using a Shimadzu UV monitor.

Results

Figure 2:
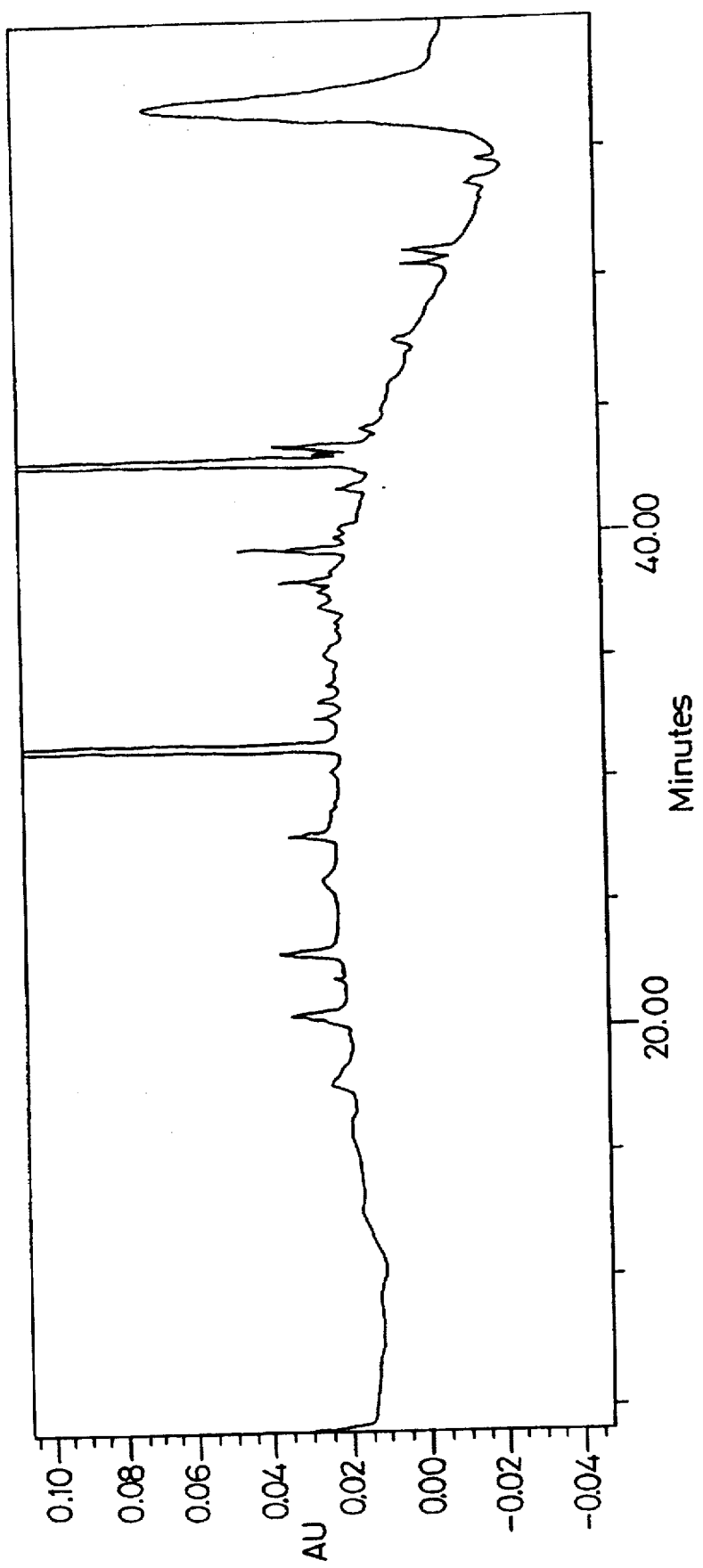
FIG. 2 is a UV trace from a C18 PTH Reverse Phase HPLC column (Applied Biosystems Inc) showing the low level of low molecular weight contaminants in albumin of the invention.

A comparison was made between a commercially available batch of human serum albumin and a batch of rHA purified according to the invention. Two main significant $A_{214\ nm}$ peaks are seen in the sample of the invention ($R_t$=31.1 and 42.8 mins respectively—see FIG. 2 and Table 9). The peak at 2.15 mins is thought to be due to insoluble or partially soluble material passing through the column, and the large peak at 56.5 mins is also present in the trace of a water blank and, thus, is regarded as an artifact.

TABLE 9

Peak Results

| # | Ret Time (min) | Area (uV*sec) | Height (uV) |
|---|---|---|---|
| 1 | 0.800 | 3459686 | 219122 |
| 2 | 1.667 | 418606 | 33569 |
| 3 | 2.150 | 77883335 | 1963630 |
| 4 | 3.000 | 6293258 | 122295 |
| 5 | 20.433 | 297608 | 14424 |
| 6 | 22.900 | 205822 | 14601 |
| 7 | 27.567 | 150851 | 10835 |
| 8 | 31.117 | 2213883 | 170938 |
| 9 | 37.983 | 164710 | 15088 |
| 10 | 39.267 | 347946 | 29879 |
| 11 | 41.750 | 107515 | 8402 |
| 12 | 42.783 | 2303024 | 192911 |
| 13 | 43.217 | 139744 | 14141 |
| 14 | 43.457 | 254521 | 23979 |
| 15 | 50.467 | 152805 | 13226 |
| 16 | 50.950 | 162364 | 12577 |
| 17 | 56.533 | 5753796 | 83674 |

Figure 3:
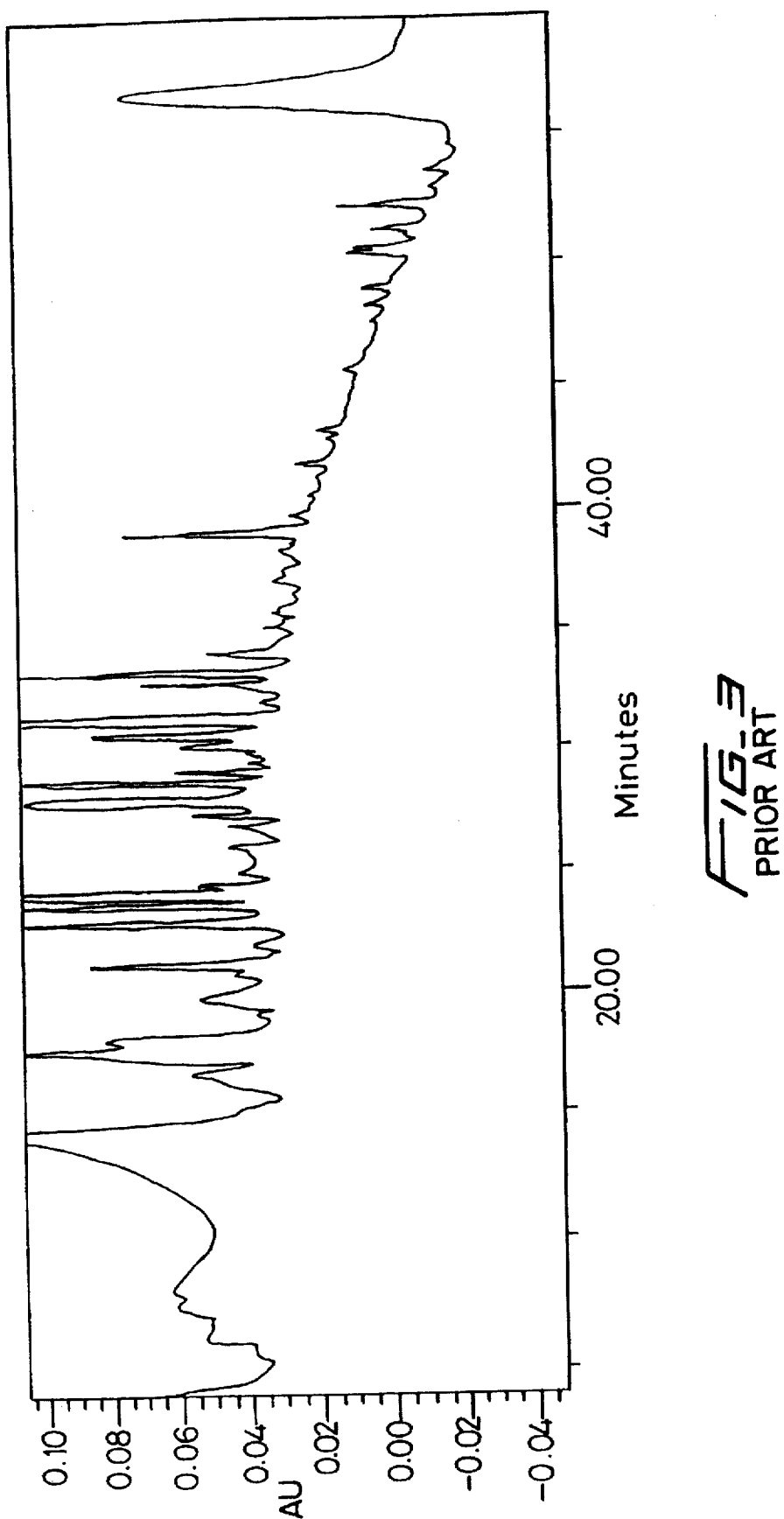
FIG. 3 is also a UV trace as FIG. 2 but illustrating the high level of low molecular weight contaminants in prior art albumin.

The commercially available HSA, on the other hand, has many more peaks (see FIG. 3) and Table 10.

TABLE 10

Peak Results

| # | Ret Time (min) | Area (uV*sec) | Height (uV) |
|---|---|---|---|
| 1 | 0.350 | 244385 | 23957 |
| 2 | 0.633 | 607880 | 45310 |
| 3 | 0.783 | 3239730 | 243477 |
| 4 | 0.983 | 1072033 | 158146 |
| 5 | 2.233 | 76773569 | 2038028 |
| 6 | 2.933 | 6634089 | 182363 |
| 7 | 3.733 | 2812688 | 95459 |
| 8 | 12.483 | 818540 | 20185 |
| 9 | 12.650 | 218748 | 22750 |
| 10 | 14.150 | 5423715 | 98336 |
| 11 | 16.333 | 423403 | 17460 |
| 12 | 16.633 | 688525 | 24538 |
| 13 | 17.550 | 2301309 | 84781 |
| 14 | 18.033 | 1145045 | 47806 |
| 15 | 19.750 | 672721 | 21562 |
| 16 | 20.233 | 87799 | 9760 |
| 17 | 20.700 | 272171 | 13003 |
| 18 | 21.100 | 862146 | 55792 |
| 19 | 21.967 | 166471 | 8928 |
| 20 | 22.883 | 1381445 | 97660 |
| 21 | 23.583 | 1112632 | 89851 |
| 22 | 24.000 | 4740347 | 419780 |
| 23 | 24.417 | 352486 | 26374 |
| 24 | 24.917 | 171279 | 14625 |
| 25 | 25.133 | 99734 | 11473 |
| 26 | 25.267 | 133911 | 10515 |
| 27 | 25.667 | 223556 | 11854 |
| 28 | 25.967 | 257295 | 17351 |
| 29 | 26.600 | 93906 | 7957 |
| 30 | 26.817 | 223113 | 18326 |
| 31 | 27.250 | 303831 | 29461 |
| 32 | 27.533 | 124218 | 12710 |
| 33 | 27.783 | 5747091 | 561629 |
| 34 | 28.550 | 1383761 | 119772 |
| 35 | 29.033 | 390986 | 33455 |
| 36 | 29.417 | 182131 | 12713 |
| 37 | 29.833 | 181333 | 12584 |
| 38 | 30.183 | 478320 | 30155 |
| 39 | 30.583 | 1048945 | 58465 |
| 40 | 31.067 | 3454425 | 214489 |
| 41 | 31.983 | 168275 | 8663 |
| 42 | 32.717 | 651406 | 43161 |
| 43 | 33.150 | 1142221 | 102588 |
| 44 | 34.017 | 420756 | 23883 |

TABLE 10-continued

| | Peak Results | | |
|---|---|---|---|
| # | Ret Time (min) | Area (uV*sec) | Height (uV) |
| 45 | 35.100 | 15704 | 10008 |
| 46 | 37.033 | 166588 | 9468 |
| 47 | 38.267 | 145731 | 8078 |
| 48 | 38.983 | 781209 | 54029 |
| 49 | 41.800 | 86967 | 8868 |
| 50 | 48.883 | 95416 | 8522 |
| 51 | 50.267 | 174159 | 16737 |
| 52 | 50.483 | 176115 | 15573 |
| 53 | 51.267 | 158727 | 13701 |
| 54 | 52.183 | 297278 | 25795 |
| 55 | 56.533 | 5846645 | 85710 |

The quality of the albumin of the invention in terms of non-covalently bound LMCs is clearly superior to that of clinical HSA. Expressed numerically, the total peak area between 10 mins and 55 mins for the albumin of the invention was about 6.4 V·sec whereas the total peak area between the same two times for commercially available material was about 39.7 V·sec.

A similar analysis was carried out with detection at 280 nm, in which case the peak area for albumin purified in accordance with the present invention was 0.56 V·sec., whereas that for commercially available HSA was 14.9 V·sec.

Analysis of fluorescent low molecular weight contaminants (excitation at 280 nm, detection at 350 nm) again revealed a total peak area for albumin purified by the process of the invention to be less than 10% of that for HSA.

Capillary Zone Electrophoresis of rHA and HSA

Capillary electrophoresis (CE) is used as an alternative to standard SDS-PAGE in order to qualitatively compare purified rHA of the invention and commercially available HSA. CE is a high resolving electrophoretic technique and is capable of separating sub-populations of the same protein when only minor differences are to be found.

Method

Samples of HSA (Armour) and rHA purified according to the invention were separated in 20 mM $PO_4/B_4O_7$ buffer, pH=7.4 at 20 KeV and 30° C. were electrophoresed on an ABI 230 CE. The rHA of the invention gave a single peak on the electrophoretogram indicative of its homogeneity. In contrast, other peaks were observed in the commercially available HSA samples. These peaks are believe to be indicative of the presence of dimeric, polymeric or glycated species.

Analysis of C-terminus

An important aspect of the quality control of recombinant proteins is the confirmation and stability of the pre-determined primary structure.

Materials and Methods

Tryptic Digestion: HSA (from a commercial source—one sample stored at -20° C. and one stored at 30° C. for 12 weeks), rHA purified according to the invention (stored at 4° C. and 30° C. for 6 months) and a Des-Leu rHA (a truncated form of rHA minus the C-terminal leucine) (1 mg each) were reduced with 5 mM dithiothreitol (Calbiochem) for 120 min 37° C., then alkylated with 10 mM iodoacetamide (Sigma) for 90 mins at 37° C. in 6M guanidine HCl in 0.5M Tris HCl pH 8.0.

The samples were then diluted 1 in 3 with $H_2O$ and digested with trypsin for 48 hours at 37° C. (TPCK treated trypsin from Sigma, 3×10 μl aliquots of 1 mg/ml solution added over 48 hours).

Peptide Mapping: Tryptic digests were mapped on reverse phase (RP) HPLC on a Gilson HPLC system using a 25 cm Pharmacia SuperPac Pep-S column (5 μm $C_2/C_{18}$). The eluents used were A, 0.1% (v/v) TFA (ABI) in water; B, 0.09% (v/v) TFA in 70% (v/v) acetonitrile (Fisons Scientific)—linear gradient over 60 min, 0.5 ml/min. UV detection at 214 nm and 280 nm.

N-terminal Sequencing: Performed on an ABI 477A protein sequencer.

Fast Atom Bombardment—Mass Spectrometry: FAB-MAS was performed on a VG Autospec by M-Scan Limited, Ascot, UK.

Peptide Synthesis: The full length C-terminal tryptic peptide LVAASQAALGL (mass 1012) was synthesised by ABI, Warrington, UK; and the truncated version LVAASQAALG (mass 899) was synthesised by the Department of Biochemistry, University of Nottingham, Nottingham, UK.

Results

The full length C-terminal tryptic peptide (mass 1012) was shown, using the synthetic marker peptide, to elute at 37.5 minutes on RP-HPLC. This peak was collected and identified by N-terminal Sequencing and FAB-MS from HSA and rHA.

Removal of the C-terminal leucine results in a truncated C-terminal peptide (mass 899) which was shown to elute at 28.5 minutes, confirmed using the synthetic marker peptide. This peak was isolated from the tryptic digest of Des-Leu rHA and identified by N-terminal Sequencing and FAB-MS. Two other peptides were shown to be present in this 28.5 minute peak, AWAVAR (mass 673) and DLGEENFK (mass 950).

The 28.5 minute peak was collected off RP-HPLC from the tryptic digests of HSA, HSA stored at 30° C. for 12 weeks, Des-Leu rHA, rHA of the invention stored at 4° C. for 6 months and rHA of the invention stored at 30° C. for 6 months.

The peak from each digest was subsequently analyzed by N-terminal Sequencing and FAB-MS along with the synthetic marker peptides.

TABLE 11

| Peptides present in 28.5 minute peak by N-terminal Sequencing. | |
|---|---|
| SAMPLE | SEQUENCE |
| Des-Leu rHA | LVAASQAALG |
| | AWAVAR |
| | DLGEENFK |
| HSA standard | AWAVAR |
| | DLGEENFK |
| | + = 5% LVAASQAALG 5–10% |
| HSA 30° C. 12 weeks | AWAVAR |
| | DLGEENFK |
| rHA 40° C. 6 months | AWAVAR |
| | DLGEENFK |
| rHA 30° C. 6 months | AWAVAR |
| | DLGEENFK |

By FAB-MS, the main signals ((M + H)⁺ molecular ions) present in the 28.5 minute peak were as shown in Table 12.

TABLE 12

| (M + H)⁺ Ions in 28.5 min Peak. | |
|---|---|
| Mixture of Synthetic Full Length and Truncated C-terminal Peptides Des-Leu rHA | 1013- LVAASQAALGL |
| | 900- LVAASQAALG |
| | 673- AWAVAR |
| | 900- LVAASQAALG |
| | 951- DLGEENFK |
| | 1028- ? |
| | 1140- ? |
| HSA Standard | 673- AWAVAR |
| | 900- LVAASQAALG |
| | 951- DLGEENFK |
| | 1028- ? |
| | 1140- ? |
| rHA 30° C. 6 months | 673- AWAVAR |
| | 900- LVAASQAALG |
| | 1028- ? |
| | 1140- ? |
| | 951- No signal |

The signals at 1026/1028 and 1140 may be fragment ions; they were not peptides that could be detected by sequence analysis.

Conclusion

The Des-Leu C-terminal tryptic peptide was detected in commercial HSA at approximately 5-10% (not quantitative), but could not be detected in the rHA of the invention, even after 6 months at 30° C. The Des-Leu peptide could not be detected in the HSA 12 weeks at 30° C., and the peak for the full length C-terminal peptide at 37.5 minutes (though not isolated) was very diminished compared to the other samples, indicating that perhaps this has undergone further C-terminal degradation.

These results indicate that the rHA, purified in accordance with the invention, has a stable and full length carboxy-terminus, whereas HSA previous available from commercial sources appears to be heterogeneous by comparison.

Colorimetric Assay for Free Thiols in Purified Human Albumin

Introduction

Ellmann's Reagent, 5,5'-dithiobis-(2-nitrobenzoate) (DTNB), is a specific and sensitive means of detecting free thiol groups such as cys-SH. The reaction can be followed by monitoring absorbance at 412 nm, which value can be used to calculate free cys-SH, to levels of less than one residue per molecule of rHA. The following solutions reagents are utilized in the assay:

5,5'-Dithiobis (2-nitrobenzoic acid) DTNB, Sigma Product No D8130.
TRIS PRE-SET pH crystals pH8.0, Sigma Product No T4753.
EDTA, disodium, Sigma Product No ED2SS.
Sodium dihydrogen phosphate dihydrate, Analar grade.
Disodium hydrogen phosphate dihydrate, Analar grade.

Buffer 1
0.1M (12.1 g) Tris-HCl; 0.01M (3.72 g) EDTA Na₂.2H₂O, pH8.0. PRESET pH crystals. Dissolve in 500 ml water and make up to 1 liter exact volume. Stable for one month at room temperature.

Buffer 2
0.05M (5.44 g) Sodium phosphate pH7.0, 2.04 g NaH₂PO₄.2H₂O. Dissolve in 500 ml water, and make up to 1 liter exact volume. Stable for 1 month at room temperature.

Reagent
0.01M (39.4 mg) DTNB in phosphate buffer. Dissolve in 10 ml buffer 2. Prepare fresh each day.

Sample
Dilute albumin to about 10.3 µM in buffer 1 (0.66 mg/ml).

Procedure

1) Set spectrophotometer cell holder thermostat to 25° C. 2) Place 1.25 ml of sample in one cuvette and 1.25 ml of buffer 1 in another 10 mm reduced volume cuvette in the sample and reference positions respectively. 3) Zero instrument at 412 nm. Set absorbance to 0.1 AU Full Scale. 4) Add 50 µl DTNB reagent to the reference cuvette, and mix briefly using a cleaned plastic stirrer. 5) Add 50 µl DTNB reagent to the sample cuvette, and mix as above. 6) Immediately start acquiring data (or start chart recorder, and follow reaction for up to 10 mins). 7) Repeat for each sample, to obtain values in triplicate. 8) Extrapolate back from the steady absorbance decay to zero time, and read off the absorbance at 412 nm ($\delta A_{412}$) (FIG. 1). 9) Calculate the sulfydryl content using the molar extinction coefficient $\epsilon_{412}=13.9$ cm² mM⁻¹.

A number of commercial HSA samples were assayed for free thiol content, the results are summarized below:

| HSA | Free Thiol (mol SH/mol HSA) |
|---|---|
| 1 | 0.29 |
| 2 | 0.22 |
| 3 | 0.35 |
| 4 | 0.05 |
| 5 | 0.08 |
| 6 | 0.46 |
| 7 | 0.36 |

These values are significantly lower than the value for albumin prepared according to the example above which is routinely assayed at 0.85-0.9 mol SH/mol rHA.

The Determination of Metal Ion Contamination in Human Albumin by Graphite Furnace Spectroscopy Standards and samples are atomized from a pyrocoated graphite tube. The atomic absorption of the sample is detected using the following conditions:

| Metal ion | Wavelength nm | Atomization temperature °C. |
|---|---|---|
| Zn | 213.9 | 1800 |
| Cu | 327.4 | 2300 |
| Fe | 248.8 | 2400 |
| Al | 309.8 | 2500 |
| Mn | 279.8 | 2200 |

Aluminum was measured using a Perkin Elmer M2100 atomic absorption spectrophotometer, a Perkin Elmer HGA-700 graphite furnace, a Perkin Elmer AS70 Autosampler with sample cups and an aluminum hollow cathode lamp. The reagents were AR grade magnesium nitrate, an aluminum standard solution (1000 ppm) and AR grade concentrated nitric acid. A 1.00% w/v magnesium nitrate solution was made up with Milli-Q water. 15 µl of aluminum standard solution was pipetted into the autosampler and diluted to 1500 µl with 0.20% nitric acid solution. The procedure is repeated with 15 µl of the solution obtained and then with 150 μL of the solution subsequently obtained, to give a 10 ppb (μg/L) aluminum solution.

An albumin sample is diluted with 0.20% nitric acid solution to give an aluminum concentration within the limits of the calibration graph. A 1:2 dilution is usually sufficient.

Magnesium is measured similarly, using a Perkin Elmer AS-51 flame autosampler and a magnesium hollow cathode lamp. A Magnesium Standard solution of 1000 ppm is diluted with Milli-Q water to give 0.1, 0.2, 0.5 and 1.0 ppm standard solutions. The atomic absorption of the sample is detected at 285.2 nm.

Copper, iron, manganese and zinc are measured in the same way as aluminum except that, for zinc, a 1.0 ppb (μg/l) standard solution is used instead of a 10 ppb solution. The concentration of metal ions was determined in ng/L and then related to the concentration of albumin (ng metal ion/g albumin). These data are presented in Table 13.

TABLE 13

Contamination Profiles of Albumin produced according to the invention

Concentration in ng/g albumin

| Chemical | Batch A | Batch B | Batch C |
|---|---|---|---|
| Aluminum | — | 85 | — |
| Copper | 3720 | 9080 | 1780 |
| Iron | 460 | 810 | 440 |
| Magnesium | 1200 | 850 | 800 |
| Zinc | 4510 | 1490 | 1790 |
| Manganese | 20 | 191 | 16 |

| Chemical | Batch D | Batch E | Batch F | Batch G |
|---|---|---|---|---|
| Aluminum | — | — | — | — |
| Copper | 660 | 2690 | 440 | 530 |
| Iron | 930 | 380 | 2720 | 1880 |
| Magnesium | — | — | — | — |
| Zinc | 1580 | 680 | 3520 | 2130 |
| Manganese | 42 | 14 | 58 | 27 |

| Chemical | Batch H | Batch I | Batch J | Batch K |
|---|---|---|---|---|
| Aluminum | 9 | 22 | 86 | 96 |
| Copper | 520 | 590 | 9920 | 8820 |
| Iron | 1010 | 670 | 1030 | 100 |
| Magnesium | 600 | <400 | 2000 | 2000 |
| Zinc | 1740 | 1040 | 4280 | 3520 |
| Manganese | 35 | 20 | 46 | 60 |

All results are expressed as total metal ion concentration.

Table 14 shows the corresponding levels of metal ions in commercial HSA.

TABLE 14

Concentrations in ng metal\g of albumin

| Chemical | Source A (UK) | Source B (UK) | Source C (Japan) | Source D (Japan) |
|---|---|---|---|---|
| Aluminum | 790 | 970 | 915 | 420 |
| Copper | 2020 | 4510 | 23840 | 580 |
| Iron | 41220 | 15200 | 23550 | 15240 |
| Magnesium | 4500 | 500 | 15000 | 54000 |
| Zinc | 7230 | 1650 | 930 | 4580 |
| Manganese | 940 | 190 | 135 | 240 |

| Chemical | Source E (UK) | Source F (USA) | Source G (France) |
|---|---|---|---|
| Aluminum | 350 | 3190 | 155 |

TABLE 14-continued

Concentrations in ng metal\g of albumin

| Chemical | Source A (UK) | Source B (UK) | Source C (Japan) | Source D (Japan) |
|---|---|---|---|---|
| Copper | 4830 | 1180 | | 7910 |
| Iron | 7910 | 25920 | | 1850 |
| Magnesium | 1500 | 500 | | 500 |
| Zinc | 1520 | 3940 | | 2130 |
| Manganese | 160 | 65 | | 80 |

It can be seen that the average level of aluminum in the product of the invention was about 60 ng/g whereas the commercial sources had 155–3190 ng/g. Likewise, the product of the invention had an average of about 948 ng/g iron (compare 1850–41,200 ng/g in prior art material), an average of 2,990 ng/g of copper (compare 580–23,840 ng/g in prior art material), an average of 1,120 ng/g of magnesium (compare 500–54,000 ng/g in prior art material), an average of 2,390 ng/g of zinc (compare 930–7,230 ng/g in prior art material, and an average of 48 ng/g manganese (compare 65 to 940 ng/g in prior art material).

Analysis of Medium and Long Chain Fatty Acids

The fatty acids profiles of albumin according to the invention and commercially available HSA were analyzed by acidic solvent extraction and gas chromatography of the free fatty acids using a C17:0 internal standard.

Equipment

Gas chromatograph (eg Shimadzu GC 9A) with flame ionisation detector; Autoinjector (e.g. Shimadzu AOC 14); Integrator/Printer (e.g. Shimadzu CR4A); HP-FFA 30×0.53 mm, 1.0 μm phase column (Hewlett Packard Ltd); Megabore Installation kit (J & W Scientific 220–1150 for GC 9A) with direct injection liner.

Reagents

Water (Milli-Q); Dichloromethane Super Purity Solvent (Romil Chemicals, Loughborough, Leics); Sodium Acetate Trihydrate Analar (BDH Ltd, Poole); Acetic Acid Glacial Analar (BDH Ltd, Poole); Human Serum Albumin Solution (Zenalb™20, Bio Products Laboratory, Elstree, Herts); Sodium Sulphate Anhydrous (Analytical Reagent); standard fatty acids from Sigma.

Solutions 0.5M Sodium Acetate Buffer pH 4.5: Sodium Acetate 6.13 g and Acetic Acid 3.30 g per 100 ml.

Free Fatty Acid standard mixtures. Weigh 5 mg of each fatty acid into separate glass vials. Dissolve each fatty acid in 1 ml Dichloromethane and transfer to three 12 ml Pyrex culture tubes respectively for short chain (C6–C14), medium chain (C16–C18) and long chain (C20–C22:1) fatty acids. Dry down mixture under a stream of nitrogen and dissolve in 1 ml Dichloromethane. Transfer 50 μl aliquots of mixture into labelled glass vials, dry under nitrogen, cap and store at −20° C.

Internal Standard Solution 1 mg/ml Heptadecanoic Acid (25.0 mg Heptadecanoic Acid/25 ml Dichloromethane).

Procedure

1. Add 50 μl Internal Standard Solution to 6 labelled 40 ml Pyrex tubes.

2. For 5% rHA add 5 ml sample. For 25% rHA use 1 ml sample and 4 ml water. Include a blank (5 ml water) and serum albumin sample (1.25 ml Zenalb™20 and 3.75 ml water). Prepare all samples in duplicate.

3. Add 2.5 ml Sodium Acetate Buffer, then 10 ml Dichloromethane to all tubes.

4. Place the capped tubes on a mechanical roller for 2 hours at room temperature.

5. Centrifuge all tubes for 5 min at 3,000 rpm in a Sorvall RT6000B centrifuge at 20° C.

6. Remove the upper aqueous phase, then working from the bottom of the tube carefully transfer the lower Dichloromethane phase into a labelled 12 ml Pyrex tube. Protein globules may hinder the removal of all the Dichloromethane phase. If this occurs add a spatula full of Anhydrous Sodium Sulphate, cap and shake.

7. Dry Dichloromethane phase under a stream of nitrogen and store under nitrogen at −20° C. until analysis.

8. Install the capillary column and set the gas chromatograph to the following conditions according to the manufacturer's instructions:

Detector: Flame ionization Carrier Gas: Nitrogen at 30 ml min$^{-1}$; Injection Volume: 0.5 µl; Column initial temperature: 70° C.; Hold: 1.5 min; Gradient 1: 20° C. min$^{-1}$ to 150° C.; Gradient 2: 4° C. min$^{-1}$ to 240° C.; Hold: 7 min; Detector Temperature: 280° C.; Setting Specific to Shimadzu GC9A are: Detector Range: 10°; Hydrogen Pressure: 0.5 kg/cm$^2$; Air Pressure: 0.5 kg/cm$^2$; Stop Time: 50 min.

9. Set up the integrator to collect data from the gas chromatograph according to the manufacturer's instructions.

10. Raise oven temperature to 245° C. and leave until a steady baseline is achieved.

11. Lower oven temperature to 70° C. and allow to equilibrate.

12. Thaw an aliquot of the Long, Medium and Short Chain Fatty Acid standards. Dissolve the Long Chain Fatty Acids in 1 ml Dichloromethane. Transfer the solution to the Medium Chain Fatty Acids and dissolve. Repeat for the Short Fatty Acids.

13. Inject the standard mixture to determine fatty acid retention times. The chromatogram produced should have very little peak tailing and have a smooth slowly rising baseline with the correct number of well resolved peaks. Caproic Acid (C6:0) should elute with a retention time of approx 6 min and Erucic Acid (C22:1) with a retention time of approx 33 min. Identify all peaks by comparison with example standard chromatogram.

14. Inject samples and collect data.

Calculations

1. Identify the internal standard peak from the blank samples. This will be the major peak with a retention time of approximately 23.5 min.

2. Calculate the Peak Area Ratios for all integrated peaks in all samples using the following formula.

$$\text{Peak Area Ratio} = \frac{\text{Peak Area}}{\text{Internal Standard Peak Area}}$$

3. Identify fatty acid peaks in rHA and HSA samples based on retention time by comparison with standards.

4. Convert all Peak Area Ratios to approximate concentrations (µg/g albumin) for both rHA and HSA samples using the following factor:

$$\text{Concentration (µg/g)} = \text{Peak Area Ratio} \times 200$$

5. For peaks identified as fatty acids convert Concentration from µg/g albumin to mol/mol albumin using the fatty acid's molecular weight and the following formula:

$$\text{Concentration (mol/mol)} = \frac{\text{Concentration (µg/g)} \times 0.0665}{\text{Fatty Acid Molecular Weight}}$$

Figure 4:
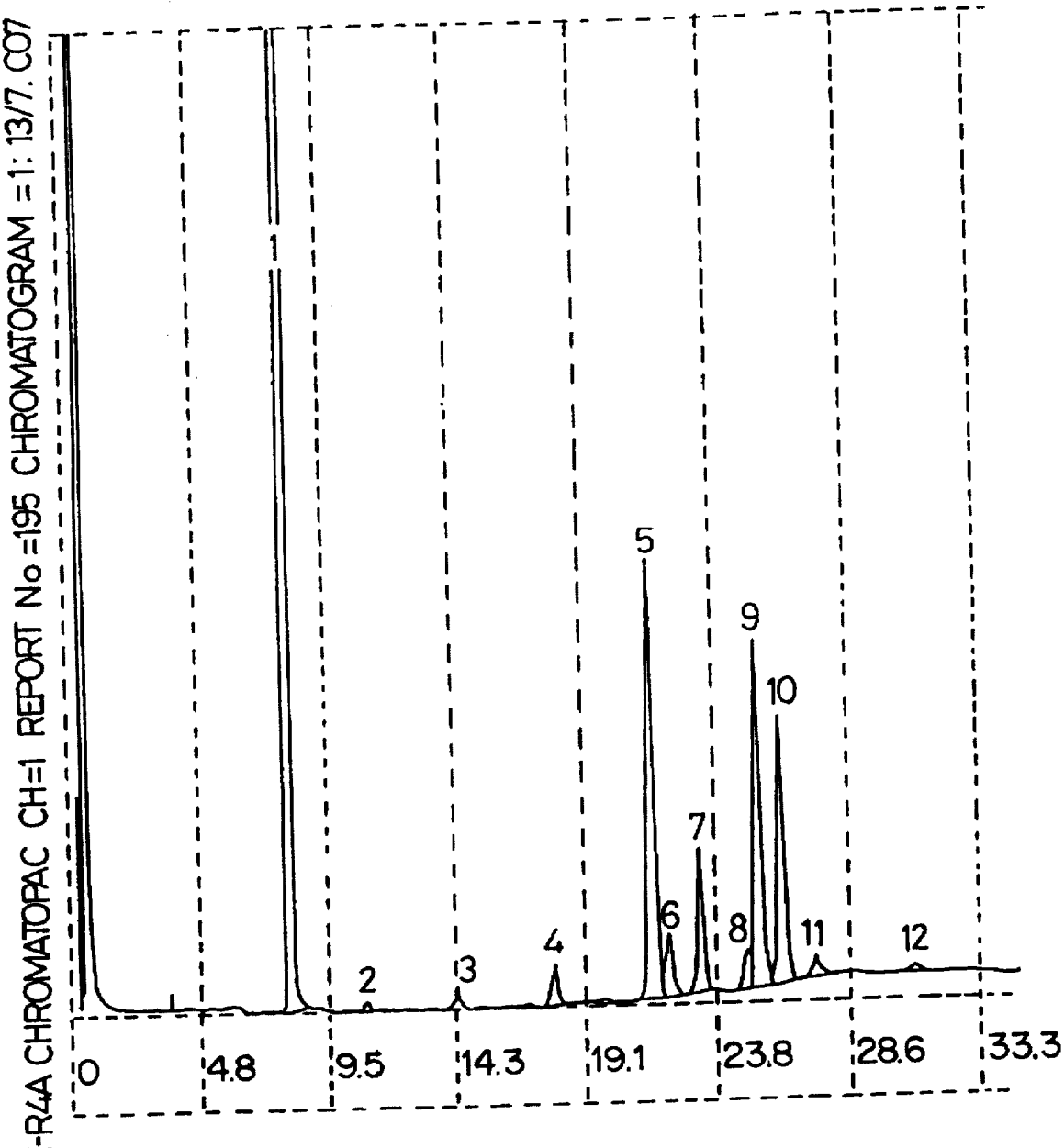
FIG. 4 is a gas chromatograph showing the fatty acid content of commercial albumin.
Figure 5:
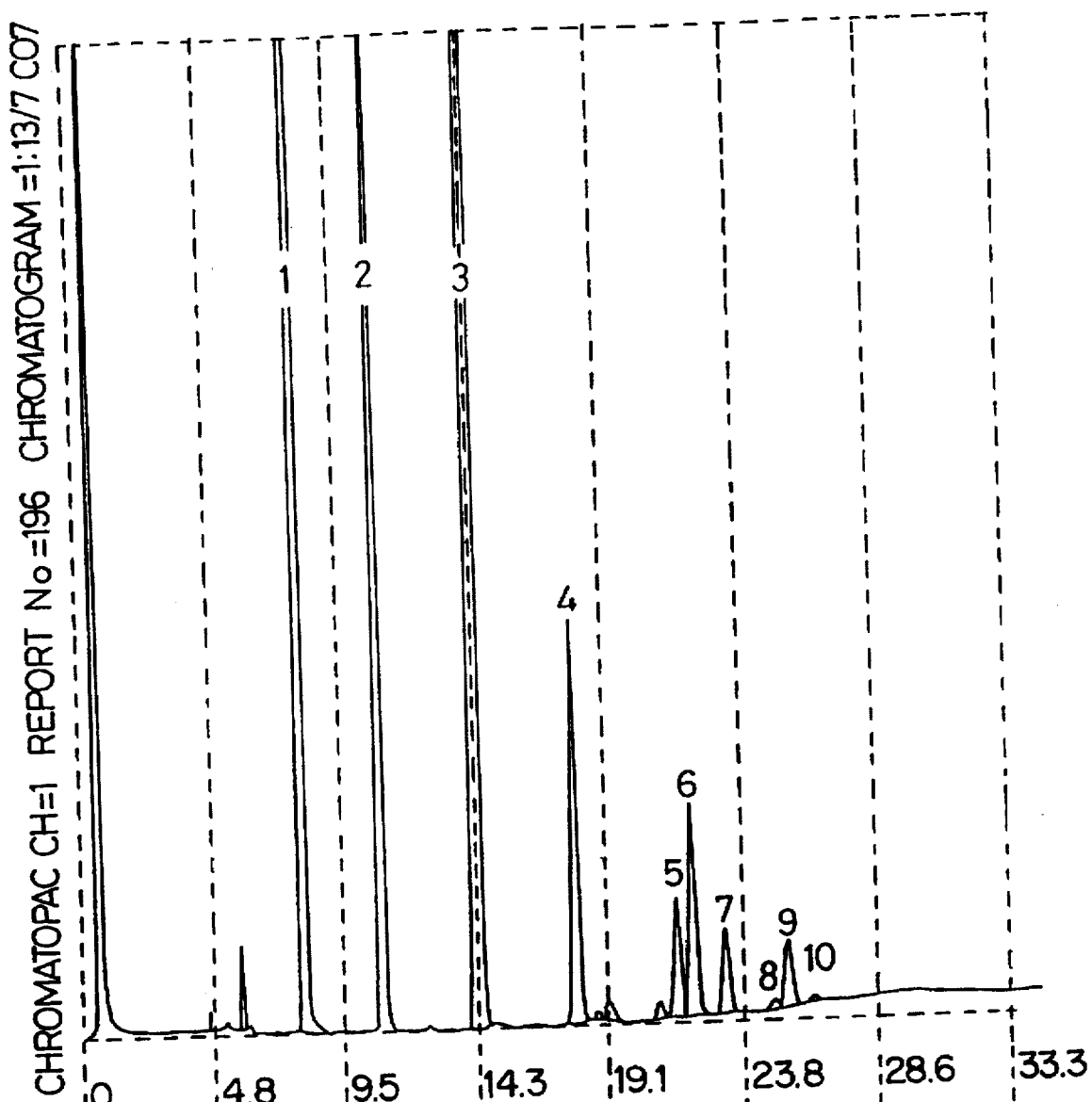
FIG. 5 is a gas chromatograph showing the fatty acid content of albumin according to the invention.

Example results are presented for a batch of albumin according to the invention (FIG. 4) and commercial HSA (FIG. 5). No abnormal fatty acids have been detected in the former by this method although the profiles for the two proteins showed significant differences. As expected, both showed large amounts of the added stabilizer, octanoate (C8:0). Apart from this, commercial HSA was characterised by predominantly C16:0, C16:1, C18:0, C18:1 and C18:2 whilst the albumin of the invention contained mainly C10:0 and C12:0 and occasionally C14:0. Further experiments showed that the levels of C10:0 and C12:0 in rHA final product correlated with the levels of these contaminants in the octanoate used for the latter stages of the purification process.

Preferably, the total level of C18 fatty acids does not exceed 1.0% (mol/mol) of the level of octanoate, and preferably does not exceed 0.5% of that level. Moreover, in the albumin of the invention, the level of C18:2, C18:3 and C20 fatty acids is generally undetectable. In commercial HSA, there may typically be about 0.4 moles C18 fatty acids per mole of albumin. In the product of the invention, there is typically no detectable C20 fatty acids and only about 0.02 moles C18 fatty acids per mole of albumin.

Analysis of Color

The absorbance of a 5% (w/v) solution of the final product in a 1 cm cuvette was measured at 350 nm, 403 nm and 500 nm and calculated in terms of absorbances per gram of albumin/liter per cm pathlength (ie ABS L·g$^{-1}$·cm$^{-1}$). The albumin of the invention has the following values:

| Wavelength (nm) | Mean absorbance (n = 10 batches) (L·g$^{-1}$·cm$^{-1}$) |
| --- | --- |
| 350 | 4.74 × 10$^{-3}$ |
| 403 | 2.12 × 10$^{-3}$ |
| 500 | 0.58 × 10$^{-3}$ |

Generally, the albumin of the invention does not exceed respective absorbances of 6.0×10$^{-3}$, 2.5×10$^{-3}$ and 0.75× 10$^{-3}$ at the said three wavelengths.

Assays of a number of commercially available HSA preparations revealed higher absorbances at these wavelengths (see Table 15)

TABLE 15

Absorbance (L·g$^{-1}$·cm$^{-1}$) of prior art HSA preparations

| SAMPLE | A$_{350}$ | A$_{403}$ | A$_{500}$ |
| --- | --- | --- | --- |
| 1 | 9.95 | 4.10 | 0.8 |
| 2 | 9.25 | 5.36 | 1.1 |
| 3 | 7.40 | 3.26 | 0.6 |
| 4 | 7.20 | 3.60 | 0.6 |
| 5 | 8.68 | 4.08 | 0.8 |
| 6 | 11.45 | 6.26 | 1.2 |
| 7 | 7.20 | 3.70 | 0.8 |
| 8 | 6.82 | 4.78 | 1.8 |

SDS Reducing Polyacrylamide Gel Electrophoresis

This assay is performed to show that rHA consists of a single polypeptide chain which when treated with a reducing agent (β-mercaptoethanol) migrates as a single band (monomer) on SDS reducing polyacrylamide electrophoresis (PAGE).

Samples of albumin were boiled in SDS reducing buffer (20 mM Tris-HCl pH 8.0 containing 2 mM EDTA, 5% (w/v) SDS and 10% (v/v) β-mercaptoethanol with the albumin at 1 mg/ml, and then separated on SDS homogeneous (12.5%) Phastgels (Pharmacia), using a loading of 1 μl of the solution. Protein bands were detected by Coomassie Blue R250 staining, scanned on a Shimadzu CS9000 densitometer. Separation of albumin showed a single band of Coomassie staining which is indicative that the proportion of albumin present as a monomer is at least 99.9%.

Gel Permeation High Pressure Liquid Chromatography

25 μl of a 10 mg/ml solution of the albumin in the eluate from the anion exchange matrix in the main embodiment of the process of the invention (i.e. where the anion exchange step is the final step before ultrafiltration and formulation) is injected onto a TSK3000SWXL column on a Shimadzu LC6A HPLC. The product was found to be at least 99.9% monomeric.

25 μl of a second 10 mg/ml solution of albumin purified in accordance with the invention which had been formulated to 25% w/v was assayed in the same manner and found to contain less than 0.1% polymeric albumin. This result indicates that the formulation as described herein has no effect on the polymer/aggregate content of the purified albumin.

Two Dimensional Gel Electrophoresis

2 μg rHA of albumin prepared by the process of the invention was subject to two-dimensional electrophoresis using a Millipore Investigator system. The separation in the first dimension was a pH 3–10 isoelectric focusing gel and was followed by a 10% polyacrylamide/SDS gel in the second dimension. On staining of the gel with Coomassie Blue, only one spot was visible, indicating the presence of only one protein species.

EXAMPLE 5

In an alternative embodiment of the process of the present invention, the albumin was eluted from the cation exchange column (for example S Sepharose FF) with a solution of octanoate (from about 1–100 mM, preferably about 5 mM, sodium octanoate) to achieve a biospecific elution. The pH should be close to the pI of the albumin for the binding of the octanoate to cause a significant overall charge difference, e.g. at least 4.5, preferably about pH 5.5. The eluate was then loaded directly onto the anion exchange resin (instead of after affinity and gel permeation chromatography) at a pH of 4.5–6.5, preferably about 5.5, and a conductivity preferably in the range 2–5 mS·cm$^{-1}$, for example about 3.5 mS·cm$^{-1}$. The eluate from the anion exchange resin (eg DE-FF) was then applied to the affinity matrix (e.g., Delta Blue Agarose as described in Example 2).

The bed height was changed from 25 cm in Example 2 to 12.5 cm to alleviate potential pressure build-up during DBA chromatography, particularly 0.5M NaOH cleaning. The reduced bed height allowed higher linear flow within normal operating pressure. Therefore, a bed height of 12.5 cm was preferred and does not adversely affect recovery of rHA or rHA purity. The linear flow-rate was doubled from 1.53 cm min$^{-1}$ in Example 2 to 3.06 cm min$^{-1}$. This linear flow-rate, facilitated by the reduced bed height, improved the throughput by a factor of four which is advantageous to the large scale plant design and was close to the maximum operating capability of the DBA. Since this linear flow rate did not appear to adversely affect recovery of rHA or rHA purity, it is preferred to utilize such a higher flow rate.

The DBA eluant remained as 2M NaCl but the pH of the eluant was changed to pH7.0 from pH9.2. The buffer was changed accordingly from 50 mM ammonium acetate to 50 mM sodium phosphate which was preferred because of its buffering at pH7.0, and its relative cost. The concentration of phosphate was preferably greater than 20 mM. The lower pH eluant was responsible for an increase in DBA eluate rHA monomer recovery. A pH lower than 7.0 increased the fragment levels, and above pH7.0 the rHA monomer recovery was compromised. The pH should be in the range 5.5–9.0, preferably pH7.0.

The eluate was then applied to the gel permeation resin, for example S-200 (HR). The S-200 running buffer was changed to 40 mM sodium phosphate pH7.0. The sodium octanoate was omitted from this buffer for cost reasons, and instead was added to the solution prior to diafiltration (added to a concentration of 1–20 mM, preferably 5 mM). The phosphate conferred a higher conductivity on the running buffer which improved the purity. A high salt concentration can be used to increase conductivity but it is still preferable to buffer the solution. The pH7.0 was preferable since this was the desired pH for formulation. The diafiltration step prior to formulation may be assisted by starting with rHA at pH7.0. The rHA was more concentrated at the final eluate than with the original process, assisting the final ultrafiltration step prior to formulation.

EXAMPLE 6

In a further embodiment of the process, the process of Example 5 was followed except that following loading of the albumin on to the cation exchange column (for example SP Sepharose FF, Pharmacia), the matrix was washed with a high salt buffer containing 1–3M NaCl, preferably 2M NaCl in sodium acetate buffer (for example 10–50 mM sodium acetate, preferably 20 mM, pH 3.5–4.5, preferably pH4.0). This more stringent washing procedure results in an eluate containing a lower level of yeast proteins. The albumin was eluted as described in Example 5.

The eluate from the cation exchange column was diluted to below 10 mS·cm$^{-1}$, preferably less than 5 mS·cm$^{-1}$, and then loaded on to an anion exchange matrix (for example DEAE Sepharose FF, Pharmacia). The anion exchange matrix was then washed with dilute borate buffer (for example 15–25 mM potassium tetraborate), which has the effect of raising the pH to approximately 9.2, and then the albumin was eluted with a more concentrated borate buffer (for example 80–150 mM potassium tetraborate, preferably 110 mM potassium tetraborate). In Examples 2 and 5, the albumin is eluted with 20 mM sodium tetraborate, 100 mM NaCl; elution with 110 mM potassium tetraborate results in an eluate with a lower content of yeast proteins, in particular yeast glycoproteins, due to an increased affinity of these species for the anion exchange matrix under these conditions. Potassium tetraborate is used in preference to sodium tetraborate because of its higher solubility. The eluate from the anion exchange matrix was then directly loaded onto an affinity matrix, e.g. Delta Blue Agarose (DBA) which was run as described in Example 5.

The eluate from the DBA matrix was then applied to a gel permeation medium, for example Sephacryl S-200 (HR) (Pharmacia) equilibrated in an ammonium acetate buffer (for example 10–100 mM, preferably about 30 mM, containing sodium chloride [20–2000 mM, preferably about 100 mM] and 1–20 mM octanoate, preferably about 5 mM octanoate). This buffer effectively exchanges the albumin into a suitable solution for the final chromatographic step, which is an affinity step to remove glycoconjugates, such as glycoproteins and glycolipids, and poly-, oligo- and monosaccharides and utilizes immobilized aminophenylboronic acid (PBA) as the ligand. The PBA is covalently coupled via a spacer to an insoluble matrix such as polyacrylamide, agarose, cellulosic or organic polymers. Preferably, the PBA is coupled to agarose (for example Matrex PBA-30 [Amicon, Inc.]). The albumin collected from the S-200 column was chromatographed through the PBA matrix, pre-equilibrated in S-200 running buffer (see above); under these conditions, the albumin does not bind appreciably to the matrix, whereas the carbohydrate-based contaminants are retarded sufficiently to separate them from the albumin as it passes through the column. The albumin solution was then adjusted to approximately pH7.0 with a suitable agent such as phosphoric acid, diafiltered, ultrafiltered and then formulated as described in Example 3.

In the above example, the cation exchange, anion exchange, DBA and PBA chromatography was carried out in radial flow columns, for example, those manufactured by Sepracor, Inc., USA.

We claim:

1. A process for preparing an albumin product at least 99.9% pure an albumin-containing solution, comprising the steps of:
   (a) passing the albumin-containing solution through a cation exchange matrix under conditions such that the albumin will bind to the matrix;
   (b) eluting from the matrix an albumin-containing cation exchange eluate;
   (c) passing the cation exchange eluate through an anion exchange matrix under conditions such that the albumin will bind to the matrix;
   (d) eluting from the anion exchange matrix an albumin-containing anion exchange eluate;
   (e) passing the anion exchange eluate through an affinity matrix comprising an albumin-binding compound;
   (f) eluting from the affinity matrix an albumin-containing affinity matrix eluate;
   (g) passing the affinity matrix eluate through a gel permeation matrix to obtain a fraction enriched in albumin.

2. A process in accordance with claim 1, wherein the fraction enriched in albumin in step (g) is passed through an affinity matrix comprising a glycoconjugate-binding and saccharide-binding compound to yield an albumin preparation depleted in glycoconjugates and saccharides.

3. A process for preparing an albumin product at least 99.9% pure from an albumin-containing solution comprising the steps of:
   (a) passing said albumin-containing solution through a cation exchange matrix under conditions such that the albumin will bind to the matrix;
   (b) eluting from said matrix an albumin-containing cation exchange eluate;
   (c) passing said eluate through an affinity matrix comprising an albumin-binding compound;
   (d) eluting from said matrix an albumin-containing affinity matrix eluate;
   (e) passing said eluate through a gel permeation matrix to obtain a fraction enriched in albumin;
   (f) passing the said albumin-enriched fraction through an anion exchange matrix under conditions such that albumin will bind to the matrix; and
   (g) eluting from said anion exchange matrix said purified albumin-containing product.

4. A process in accordance with claim 3, wherein said albumin-containing solution is a yeast culture medium obtained by culturing yeast transformed with an albumin-encoding nucleotide sequence in a fermentation medium, whereby said yeast expresses and secretes albumin.

5. A process in accordance with claim 4, wherein said fermentation medium is characterized by being free of ethylene diamine tetraacetic acid or a salt thereof.

6. A process in accordance with claim 4, wherein, prior to step (a), the yeast are separated from the fermentation medium before application to the cation exchange matrix.

7. A process in accordance with claim 3, wherein, prior to step (a), the albumin-containing solution is conditioned by adding octanoate thereto to a final concentration of from about 1–10 mM and adjusting the pH to about 4.0–5.0.

8. A process in accordance with claim 3, wherein said albumin-binding compound in said affinity matrix is a dye represented by the formula:

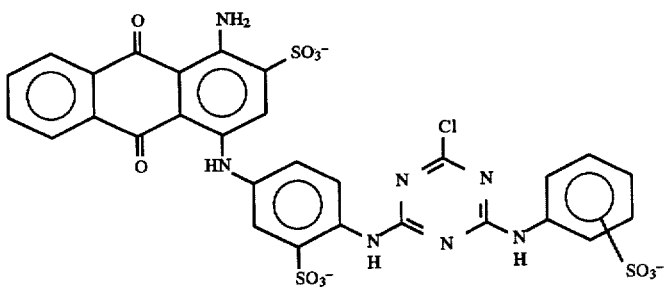

9. A process in accordance with claim 3, wherein the affinity matrix eluate obtained in step (d) is ultrafiltered through an ultrafiltration membrane to obtain an albumin-containing first ultrafiltration retentate, which is applied to the gel permeation matrix in step (e).

10. A process in accordance with claim 3, wherein said purified albumin-containing product is ultrafiltered through an ultrafiltration membrane to obtain an ultrafiltration retentate having an albumin concentration of at least about 80 g albumin per liter and said ultrafiltration retentate is diafiltered against at least 5 retentate equivalents of water.

11. A process in accordance with claim 3, wherein, in step (e), passing said retentate through said gel permeation matrix yields first and second fractions, said first fraction containing a lower concentration of albumin than said second fraction, wherein said first fraction is ultrafiltered through an ultrafiltration membrane to obtain a concentrated recycle fraction having an albumin concentration of 50–130 g albumin per liter, said recycle fraction is recycled through said gel permeation matrix to obtain further first and second fractions with lower and higher albumin concentrations, respectively, said two second fractions being pooled, said recycling step is repeated until essentially all of this albumin present in said first ultrafiltration retentate is obtained in said pooled fractions to provide said albumin-enriched fraction for step (f).

12. A process in accordance with claim 11, wherein, each said first fraction is ultrafiltered through a further ultrafiltration membrane to concentrate the albumin content to about 50–130 g albumin per liter before recycling through said gel permeation matrix.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
      ( A ) ORGANISM: Peptide fragment of human serum albumin ( x i ) SEQUENCE DESCRIPTION: SEQ ID NO:1:

Leu Val Ala Ala Ser Gln Ala Ala Leu Gly
1               5                   10

( 2 ) INFORMATION FOR SEQ ID NO:2:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
      ( A ) ORGANISM: Peptide fragment of human serum albumin ( x i ) SEQUENCE DESCRIPTION: SEQ ID NO:2:

Ala Trp Ala Val Ala Arg
1               5

( 2 ) INFORMATION FOR SEQ ID NO:3:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide (i i i) HYPOTHETICAL: NO (i v) ANTI-SENSE: NO (v) FRAGMENT TYPE: internal (v i) ORIGINAL SOURCE:
(A) ORGANISM: Peptide fragment of human serum albumin (x i) SEQUENCE DESCRIPTION: SEQ ID NO:3:

Asp Leu Gly Glu Glu Asn Phe Lys
1               5

(2) INFORMATION FOR SEQ ID NO:4:

(i) SEQUENCE CHARACTERISTICS:
(A) LENGTH: 11 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
(A) ORGANISM: Peptide fragment of human serum albumin (x i) SEQUENCE DESCRIPTION: SEQ ID NO:4:

Leu Val Ala Ala Ser Gln Ala Ala Leu Gly Leu
1               5                   10